(12) United States Patent
Kishimoto et al.

(10) Patent No.: US 9,113,791 B2
(45) Date of Patent: Aug. 25, 2015

(54) ELECTRONIC BLOOD PRESSURE MONITOR CALCULATING AVERAGE VALUE OF BLOOD PRESSURE

(75) Inventors: Hiroshi Kishimoto, Kyoto (JP); Yukiya Sawanoi, Nara (JP); Takahide Tanaka, Otsu (JP); Kenji Eda, Suita (JP)

(73) Assignee: OMRON HEALTHCARE Co., Ltd., Kyoto-shi, Kyoto (JP)

( * ) Notice: Subject to any disclaimer, the term of this patent is extended or adjusted under 35 U.S.C. 154(b) by 1489 days.

(21) Appl. No.: 11/501,726

(22) Filed: Aug. 10, 2006

(65) Prior Publication Data

US 2007/0038129 A1    Feb. 15, 2007

(30) Foreign Application Priority Data

Aug. 12, 2005   (JP) ................................. 2005-234458

(51) Int. Cl.
| | | |
|---|---|---|
| A61B 5/02 | (2006.01) | |
| A61B 5/022 | (2006.01) | |
| A61B 5/021 | (2006.01) | |
| G06F 19/00 | (2011.01) | |
| A61B 5/00 | (2006.01) | |

(52) U.S. Cl.
CPC ................ *A61B 5/022* (2013.01); *A61B 5/021* (2013.01); *A61B 5/02108* (2013.01); *G06F 19/3406* (2013.01); *A61B 5/72* (2013.01); *A61B 5/7275* (2013.01)

(58) Field of Classification Search
USPC ................................................ 600/485, 481
See application file for complete search history.

(56) References Cited

U.S. PATENT DOCUMENTS

| | | | | |
|---|---|---|---|---|
| 4,944,305 | A | | 7/1990 | Takatsu et al. |
| 5,505,206 | A | * | 4/1996 | Walloch ......................... 600/494 |
| 5,752,913 | A | * | 5/1998 | Oka .............................. 600/300 |
| 5,772,601 | A | * | 6/1998 | Oka et al. ...................... 600/495 |
| 5,836,887 | A | * | 11/1998 | Oka et al. ...................... 600/494 |
| 6,304,133 | B1 | * | 10/2001 | Sato .............................. 327/552 |
| 6,331,162 | B1 | * | 12/2001 | Mitchell ........................ 600/485 |
| 6,699,195 | B2 | * | 3/2004 | Nakazawa et al. ............. 600/485 |
| 7,367,952 | B2 | * | 5/2008 | Sawanoi et al. ............... 600/490 |
| 7,775,984 | B2 | * | 8/2010 | Kishimoto et al. ........... 600/485 |

(Continued)

FOREIGN PATENT DOCUMENTS

| | | |
|---|---|---|
| CN | 1650798 | 8/2005 |
| EP | 1 561 419 A2 | 8/2005 |

(Continued)

OTHER PUBLICATIONS

TW Office Action mailed Dec. 7, 2009, directed to counterpart TW Application No. 095129302; 4 pages.

(Continued)

*Primary Examiner* — Patricia Mallari
*Assistant Examiner* — Karen Toth
(74) *Attorney, Agent, or Firm* — Morrison & Foerster LLP

(57) ABSTRACT

Measured blood pressure data is stored in a memory in association with information related to a measurement time. In response to manipulation of a manipulation portion (memory recall switch), blood pressure data associated with the measurement time within a prescribed time period (for example, 10 minutes) from the measurement time of reference blood pressure data, among the blood pressure data stored in the memory, is retrieved as specific data. Then, an average value is calculated based on the specific data, and the calculated average value is displayed as an evaluation index.

21 Claims, 16 Drawing Sheets

(56) References Cited

U.S. PATENT DOCUMENTS

| | | | |
|---|---|---|---|
| 2004/0167417 A1* | 8/2004 | Schulhauser et al. | 600/513 |
| 2004/0176692 A1 | 9/2004 | Kario et al. | |
| 2005/0171442 A1 | 8/2005 | Shirasaki et al. | |
| 2010/0210954 A1* | 8/2010 | Bennett et al. | 600/485 |

FOREIGN PATENT DOCUMENTS

| | | |
|---|---|---|
| JP | 06-217949 A | 8/1994 |
| JP | 2002-102184 | 4/2002 |
| JP | 2002-102184 A | 4/2002 |
| JP | 2005-34470 | 2/2005 |
| RU | 2 257 140 C2 | 7/2005 |
| TW | 552127 | 9/2003 |

OTHER PUBLICATIONS

CN Office Action mailed Dec. 25, 2009, directed to counterpart CN Application No. 2006101109967; 6 pages.

Decision on Grant mailed on Jan. 10, 2008, directed to Russian Patent Application No. 2006129231/14(031766). 24 pages.

Japanese Decision to Grant Patent mailed Jan. 18, 2011, directed to counterpart Japanese Patent Application No. 2005-234458; 6 pages.

Search Report dated Sep. 20, 2013, directed to EP Application No. 06016353.2; 5 pages.

\* cited by examiner

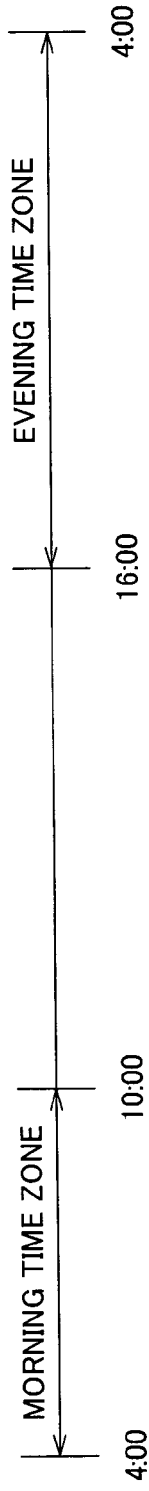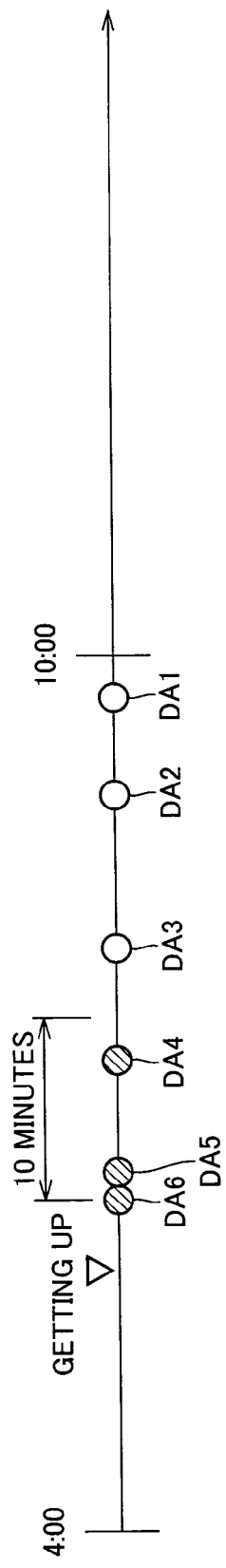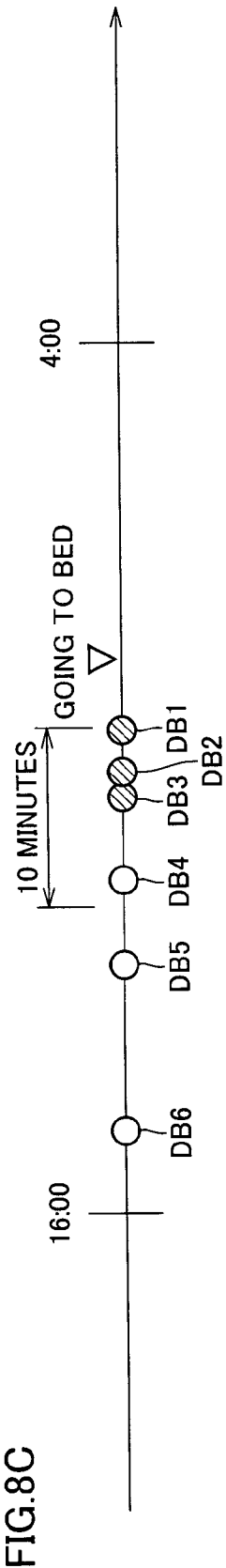

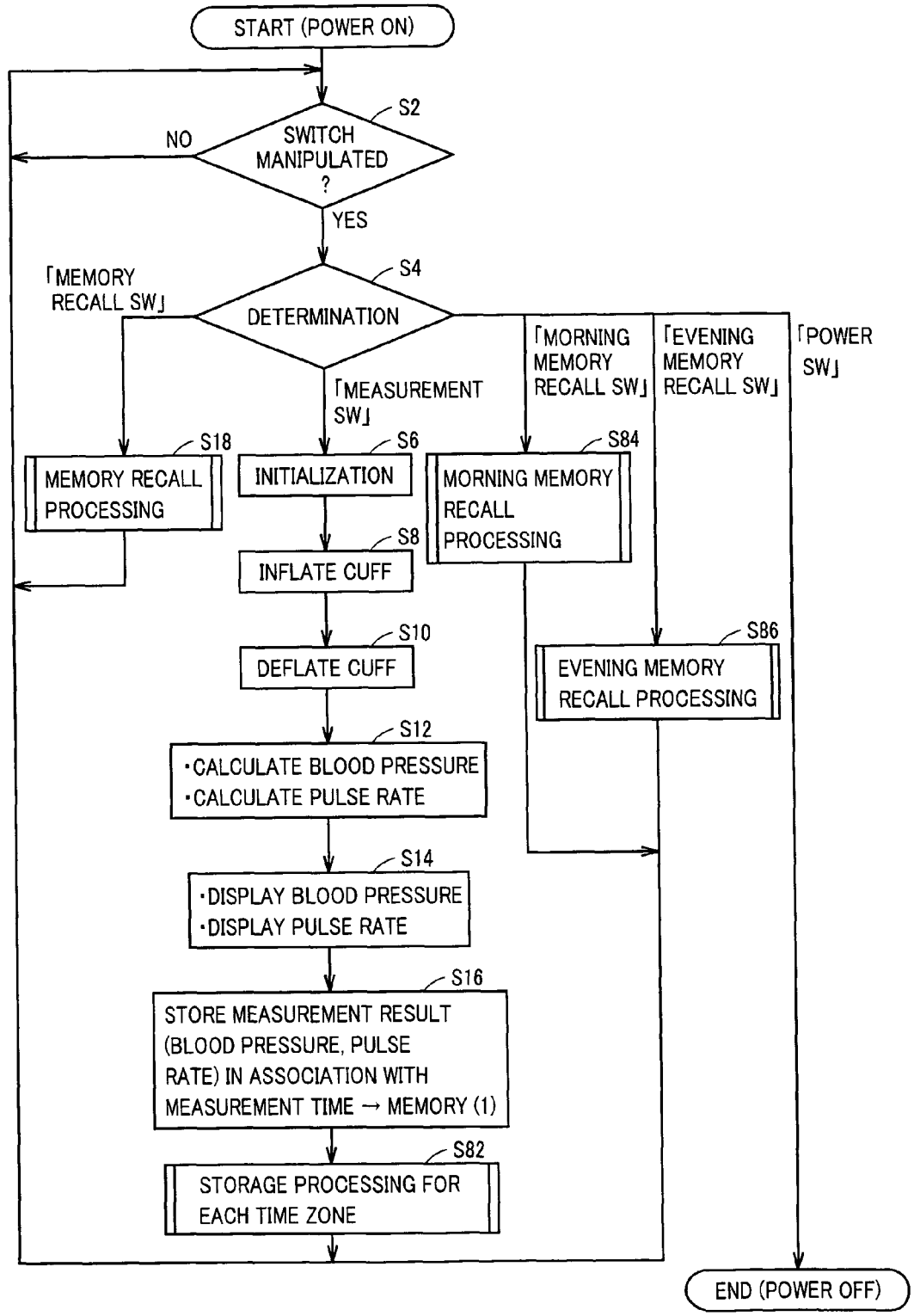

ELECTRONIC BLOOD PRESSURE MONITOR CALCULATING AVERAGE VALUE OF BLOOD PRESSURE

BACKGROUND OF THE INVENTION

1. Field of the Invention

The present invention relates to an electronic blood pressure monitor, and more particularly to an electronic blood pressure monitor capable of calculating an average value of measured blood pressure data.

2. Description of the Background Art

In recent years, many people suffer from lifestyle diseases caused by hypertension, and blood pressure management using a blood pressure level as an index for health care is important. The blood pressure, however, readily fluctuates depending on life environment and stress. Therefore, in blood pressure measurement, trend management or a management method using an average value, without nervously reacting to a blood pressure level for each measurement, is useful. As such, the following techniques have conventionally been proposed.

For example, according to the disclosure of Japanese Patent Laying-Open No. 2002-102184, inflation/deflation of an air bag (cuff) is automatically repeated for two or more cycles, preferably three cycles, and respective average values of maximal blood pressure (systolic blood pressure), minimal blood pressure (diastolic blood pressure) and pulse rate/minute measured for each cycle as well as a maximum deviation between the measured value and the average value are automatically calculated and displayed at the end of the last cycle. In addition, according to the disclosure, the number of cycles to be repeated can be set in advance.

Moreover, Japanese Patent Laying-Open No. 06-217949 discloses the following technique. Specifically, blood pressure is successively measured at each measurement point first predefined number of times in a relatively short period of time during which fluctuation of blood pressure caused by a living body is less likely. If fluctuation of the blood pressure levels obtained by measurement conducted first predefined number of times or obtained by measurement conducted second predefined number of times not as great as the first predefined number of times is within a predefined range, it is determined that reliable measurement has been conducted. If it is determined that measurement is reliable, an average value of the blood pressure levels obtained by measurement conducted second predefined number of times is employed as measurement data, and a circadian rhythm regression curve of the blood pressure is found. On the other hand, if fluctuation of the blood pressure levels obtained by measurement conducted the second predefined number of times is not within a predefined range in repeated measurement conducted first predefined number of times, the blood pressure levels as many as the second predefined number, of which value is close to that of the blood pressure levels obtained by measurement conducted first predefined number of times, are selected from the blood pressure levels obtained by measurement conducted first predefined number of times, the average value of the selected blood pressure levels is employed as measurement data, and a circadian rhythm regression curve of the blood pressure is found.

According to the techniques as described above, however, data including data chronologically measured when a mental and physical condition of a subject or an ambient environment is different are averaged, and that average is used as the evaluation index. In addition, a time period during which the subject is engaged in successive measurement becomes longer, which leads to lower blood pressure measurement compliance of the subject.

SUMMARY OF THE INVENTION

From the foregoing, the present invention was made to solve the above-described problems, and an object of the present invention is to provide an electronic blood pressure monitor capable of useful blood pressure management while maintaining blood pressure measurement compliance of a subject.

In order to achieve the object above, an electronic blood pressure monitor according to one aspect of the present invention includes: a measurement unit for measuring blood pressure of a subject; a time counting unit for counting time; a memory unit for storing measured blood pressure data in association with information related to a measurement time; a manipulation portion manipulated by the subject; a first retrieving unit for retrieving, as specific data, the blood pressure data associated with the measurement time within a prescribed time period from a measurement time of reference blood pressure data, among the blood pressure data stored in the memory unit; an average value calculation unit for calculating an average value based on the specific data; a generation unit generating a signal for displaying calculated average value as an evaluation index; and a display unit for display corresponding to the signal generated by the generation unit.

In this manner, in response to manipulation of the manipulation portion by the subject, the average value is calculated and displayed based on the blood pressure data measured within the prescribed time period from the measurement time of the reference blood pressure data.

Preferably, the memory unit stores the measured blood pressure data and the measurement time in association with each other.

Preferably, the first retrieving unit includes a first selection unit for selecting a prescribed plurality of pieces of blood pressure data among the specific data, and the average value calculation unit calculates an average value of the blood pressure data selected by the first selection unit.

Preferably, the first selection unit selects all of the specific data, if the number of pieces of the specific data is smaller than the number of the prescribed plurality of pieces of blood pressure data.

In this manner, even if there is only a single piece of blood pressure data measured within the prescribed time period from the measurement time of the reference blood pressure data, that is, even if there is only reference blood pressure data, the value of the reference blood pressure data is displayed as the result of calculation by the average value calculation unit.

Preferably, it is predetermined that the reference blood pressure data is the most recent blood pressure data, and the first retrieving unit retrieves, as the specific data, blood pressure data associated with a measurement time within the prescribed time period from a measurement time of the most recent blood pressure data.

Alternatively, preferably, it is predetermined that the reference blood pressure data is the oldest blood pressure data, and the first retrieving unit retrieves, as the specific data, blood pressure data associated with a measurement time within the prescribed time period from a measurement time of the oldest blood pressure data.

Further alternatively, preferably, it is predetermined that the reference blood pressure data is blood pressure data designated by the subject, and the first retrieving unit retrieves, as the specific data, blood pressure data associated with a measurement time within the prescribed time period from a measurement time of the designated blood pressure data.

Preferably, the manipulation portion includes a manipulation switch provided in order to recall information on the blood pressure data stored in the memory unit, and the reference blood pressure data is specified in response to pressing of the manipulation switch.

Preferably, the first retrieving unit includes a second selection unit for selecting from the specific data, blood pressure data within a prescribed allowable range of fluctuation from a reference blood pressure value, and the first average value calculation unit calculates an average value of the blood pressure data within the prescribed allowable fluctuation range selected by the second selection unit.

Here, the allowable fluctuation range may be predetermined or may be set by the subject.

Preferably, it is predetermined that the reference blood pressure value is a blood pressure value corresponding to any one of the oldest blood pressure data, the most recent blood pressure data, and the blood pressure data designated by the subject, among the specific data.

Alternatively, it may be predetermined that the reference blood pressure value is an average value of the specific data.

Preferably, the electronic blood pressure monitor further includes: a second retrieving unit for retrieving, as intended blood pressure data, blood pressure data stored in association with a measurement time within the prescribed time period from the measurement time of the measured blood pressure data for each blood pressure measurement; a blood pressure data piece number determination unit for determining whether a prescribed plurality of pieces of blood pressure data within a prescribed allowable range of fluctuation from a reference blood pressure value are present among the intended blood pressure data; and a notification unit for urging measurement again upon the subject if the blood pressure data piece number determination unit determines that there are not blood pressure data as many as the prescribed plurality of pieces.

Alternatively, the electronic blood pressure monitor further includes: a second retrieving unit for retrieving, as intended blood pressure data, blood pressure data stored in association with a measurement time within the prescribed time period from the measurement time of the measured blood pressure data for each blood pressure measurement; and a blood pressure data piece number determination unit for determining whether a prescribed plurality of pieces of blood pressure data within a prescribed allowable range of fluctuation from a reference blood pressure value are present among the intended blood pressure data; and measurement of blood pressure by the measurement unit may be repeated until the blood pressure data piece number determination unit determines that the prescribed plurality of pieces of blood pressure data are present.

Preferably, it is predetermined that the reference blood pressure value is a blood pressure value corresponding to any one of the oldest blood pressure data, the most recent blood pressure data, and the blood pressure data designated by the subject, among the intended blood pressure data.

Alternatively, it is preferably predetermined that the reference blood pressure value is an average value of the intended blood pressure data.

Preferably, the electronic blood pressure monitor further includes: a sensing unit for sensing interruption of continuity among a plurality of pieces of blood pressure data measured within the prescribed time period; and an excluding unit for excluding from the specific data, blood pressure data before or after a time at which interruption event is sensed by the sensing unit, and the average value calculation unit calculates an average value of the blood pressure data after exclusion by the excluding unit.

In this manner, even if there are a plurality of pieces of blood pressure data measured within the prescribed time period, the average value of solely blood pressure data assumed to have continuity is calculated.

Preferably, the measurement unit includes a cuff that can be placed on a blood pressure measurement site, a pressure application/reduction unit for regulating a pressure to be applied to the cuff, a pressure detection unit for detecting a pressure in the cuff, and a blood pressure calculation unit for calculating blood pressure based on a signal obtained in the pressure detection unit, and the sensing unit senses placement and removal of the cuff as the interruption of continuity.

Alternatively, the sensing unit preferably senses an ON/OFF signal from the manipulation portion as interruption of continuity.

Alternatively, the electronic blood pressure monitor further includes a cover connected to a main unit of the electronic blood pressure monitor in a freely opening/closing manner, and the sensing unit preferably senses opening/closing of the cover as interruption of continuity.

Preferably, the electronic blood pressure monitor further includes: a first time zone determination unit for determining whether a measurement time is included in a prescribed time zone for each blood pressure measurement; a third selection unit for selecting blood pressure data measured within the prescribed time period from a measurement time of the reference blood pressure data, if the first time zone determination unit determines that the measurement time is included in the prescribed time zone; and a storing operation unit for storing blood pressure data selected by the third selection unit in the memory unit in association with the prescribed time zone.

In this manner, in response to manipulation of the manipulation portion by the subject, the average value of solely blood pressure data measured within the prescribed time period in the prescribed time zone is calculated and displayed.

Preferably, it is predetermined that the reference blood pressure data is the most recent blood pressure data in the prescribed time zone, and the storing operation unit stores a prescribed plurality of pieces of blood pressure data in the memory unit sequentially from the most recent blood pressure data in a reverse chronological order.

Preferably, the prescribed time zone here is the time zone corresponding to evening (before going to bed).

Preferably, it is predetermined that the reference blood pressure data is the oldest blood pressure data in the prescribed time zone, and the storing operation unit stores a prescribed plurality of pieces of blood pressure data in the memory unit sequentially from the oldest blood pressure data in a chronological order.

Preferably, the prescribed time zone here is the time zone corresponding to morning (after getting up).

Preferably, the storing operation unit stores all blood pressure data measured in the prescribed time zone in the memory unit, if the number of pieces of blood pressure data measured in the prescribed time zone is smaller than the number of prescribed plurality of pieces of blood pressure data.

Preferably, the electronic blood pressure monitor further includes: a second time zone determination unit for determining whether the measurement time is included in any one of a prescribed plurality of time zones for each blood pressure measurement; a fourth selection unit for selecting, as the specific data, blood pressure data measured within the prescribed time period from a measurement time of the reference blood pressure data in the time zone including the measurement time, if the second time zone determination unit determines that the measurement time is included in any of the time zones; and a storing operation unit for storing the specific data selected by the fourth selection unit in the memory unit in association with a measurement day and a specific time zone.

Preferably, the manipulation portion includes a plurality of manipulation switches provided to recall an average value of the specific data associated with each of the plurality of time zones in the memory unit. When the same manipulation switch out of the plurality of manipulation switches is pressed successively, the average value calculation unit calculates an average value in a corresponding time zone successively on a day-to-day basis every time the same manipulation switch is pressed. When another manipulation switch is pressed after the same manipulation switch is pressed, the average value calculation unit calculates an average value in a second time zone corresponding to another manipulation switch, included in any of the same day, next day and previous day of a day of measurement of the specific data of which average value has been calculated immediately before.

Preferably, the prescribed time period can be set by the subject.

Preferably, the electronic blood pressure monitor further includes: a time measuring unit for measuring a prescribed time interval based on time data from the time counting unit; and a repeating unit for repeating blood pressure measurement by the measurement unit prescribed times, each time the prescribed time interval elapses within the prescribed time period.

Preferably, the electronic blood pressure monitor further includes a setting unit for setting the time interval and the number of times of blood pressure measurement in the repeating unit, and the prescribed time period is a time period determined based on the time interval and the number of times.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 8A to 8C illustrate data selection for calculating an average value in a second embodiment of the present invention.

FIG. 9 is a flowchart of a main routine executed by the CPU in the electronic blood pressure monitor according to the second embodiment of the present invention.

DESCRIPTION OF THE PREFERRED EMBODIMENTS

Figure 1:
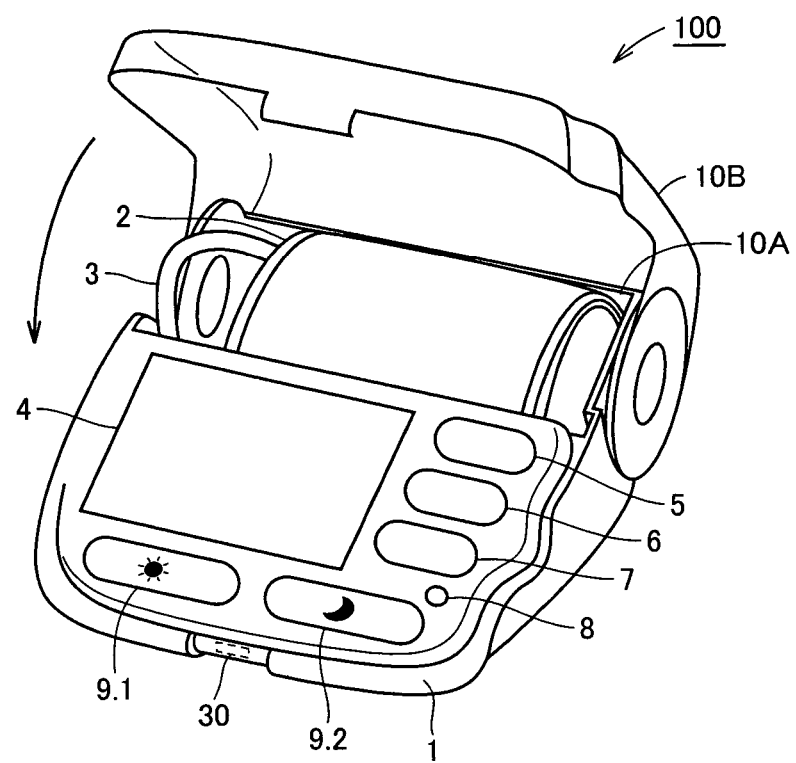
FIG. 1 is a schematic view of an electronic blood pressure monitor according to first to fifth embodiments of the present invention.

An embodiment of the present invention will be described in detail with reference to the drawings. In the drawing, the same or corresponding elements have the same reference characters allotted.

First Embodiment

Referring to FIG. 1, an electronic blood pressure monitor 100 according to the first embodiment includes a blood pressure monitor main unit 1, a cuff 2 placed on a blood pressure measurement site of the subject and applying pressure using air pressure, an air tube 3 connecting blood pressure monitor main unit 1 and cuff 2 to each other, a storage space 10A in which cuff 2 and air tube 3 can be stored, and a cover 10B connected to blood pressure monitor main unit 1 in a freely opening/closing manner. Cover 10B is connected to a side surface in the rear of blood pressure monitor main unit 1 by means of a hinge, and cover 10B can cover storage space 10A and the entire upper surface of blood pressure monitor main unit 1. Alternatively, cover 10B may cover solely storage space 10A. Cover 10B can be opened/closed by the subject.

Blood pressure monitor main unit 1 has a display unit 4 provided in order to allow the subject to view the display content, a power switch 5 provided in a manner externally operable by the subject, a measurement switch 6, a memory recall switch 7, and a time setting switch 8. A morning memory recall switch 9 and an evening memory recall switch 9.2 shown in FIG. 1 will be described in a second embodiment later.

Power switch 5 is manipulated in order to turn ON/OFF the power of blood pressure monitor main unit 1. Measurement switch 6 is manipulated in order to instruct start of blood pressure measurement. Memory recall switch 7 is manipulated in order to recall information on stored blood pressure data. Time setting switch 8 is manipulated in order to set the time.

Figure 2:
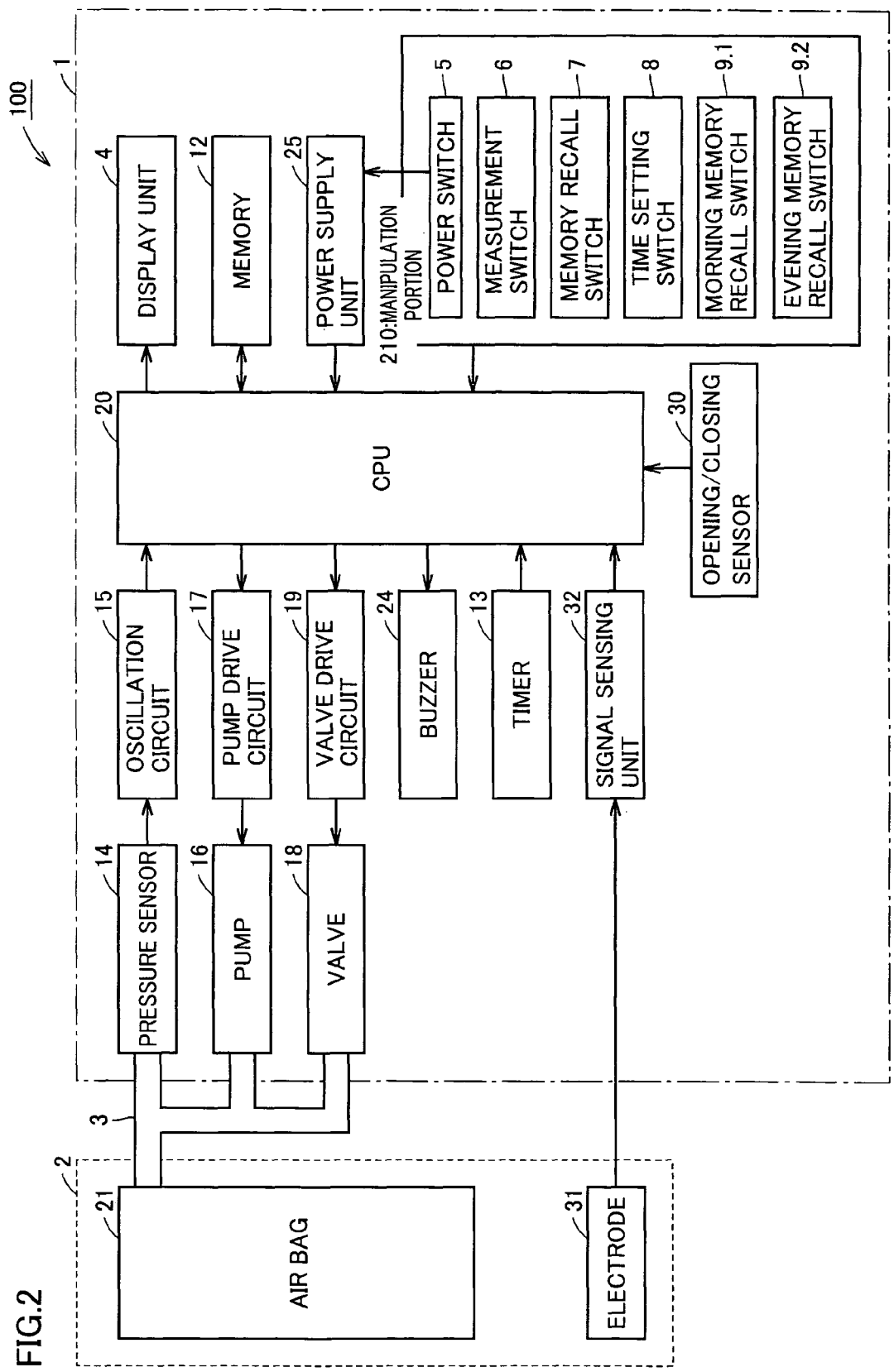
FIG. 2 is a block diagram of the electronic blood pressure monitor according to the first to fifth embodiments of the present invention.

FIG. 2 shows an internal configuration of blood pressure monitor main unit 1. Referring to FIG. 2, blood pressure monitor main unit 1 includes a pressure sensor 14 of which capacity varies in accordance with a pressure in an air bag 21 (hereinafter, referred to as "cuff pressure") contained in cuff 2, an oscillation circuit 15 outputting a signal of oscillation frequency in accordance with the capacitance value of pressure sensor 14 to a CPU (Central Processing Unit) 20, a pump 16 and a valve 18 for regulating a cuff pressure level, a pump drive circuit 17 driving pump 16, a valve drive circuit 19 for adjusting a position of valve 18, CPU 20 for intensively controlling and monitoring each component, display unit 4, a memory 12 storing various types of data and programs, a manipulation portion 210 that can be manipulated by the subject, a timer 13 operating to time and outputting time data, a buzzer 24, and a power supply unit 25 for supplying power. Air bag 21 is connected to pressure sensor 14, pump 16 and valve 18 through air tube 3. CPU 20 converts a signal received from oscillation circuit 15 to a pressure signal, thereby sensing the pressure.

Manipulation portion 210 includes power switch 5, measurement switch 6, memory recall switch 7, time setting switch 8, morning memory recall switch 9.1, and evening memory recall switch 9.2 shown in FIG. 1. Manipulation portion 210 is implemented by a plurality of switches in the present embodiment, however, it is not limited as such.

In the configuration described above, in measuring the blood pressure, CPU 20 applies a prescribed algorithm to data of pressure sensed based on a signal from oscillation circuit 15, so as to calculate blood pressure values, that is, systolic blood pressure and diastolic blood pressure as well as pulse rate. A well-known procedure that has conventionally been provided is applicable as the procedure for such measurement. The blood pressure value, or the blood pressure value and the pulse rate calculated in such a manner may be hereinafter also referred to as "measurement value". In the present embodiment, under the control of CPU 20, the measurement value is stored in memory 12 in association with the measurement time for each blood pressure measurement. In addition, CPU 20 generates a signal for displaying the measurement value, so that display unit 4 displays the measurement value.

In blood pressure management, it is desirable to measure the blood pressure several times within a short period of time and to employ an average value of the measurement values for blood pressure management. Accordingly, electronic blood pressure monitor 100 according to the present embodiment attains a function to calculate the average value. On the other hand, for example, if immediately preceding three measurement values stored in memory 12 are simply averaged, the following disadvantage arises. Specifically, if the subject measures blood pressure several times in the previous evening and measures blood pressure only twice in the morning of that day, the average value of two measurement values on that day and one measurement value in the previous evening is calculated. This is not preferred as a method of calculating the evaluation index of the blood pressure that sensitively fluctuates depending on an ambient environment and a mental and physical condition of the subject. Therefore, in electronic blood pressure monitor 100 according to the present embodiment, solely the measurement values obtained within a prescribed time period (for example, 10 minutes) from the measurement time associated with the most recent (immediate) measurement value stored in memory 12 are used for calculating the average value. The disadvantage as described above can thus be overcome.

Figure 18:
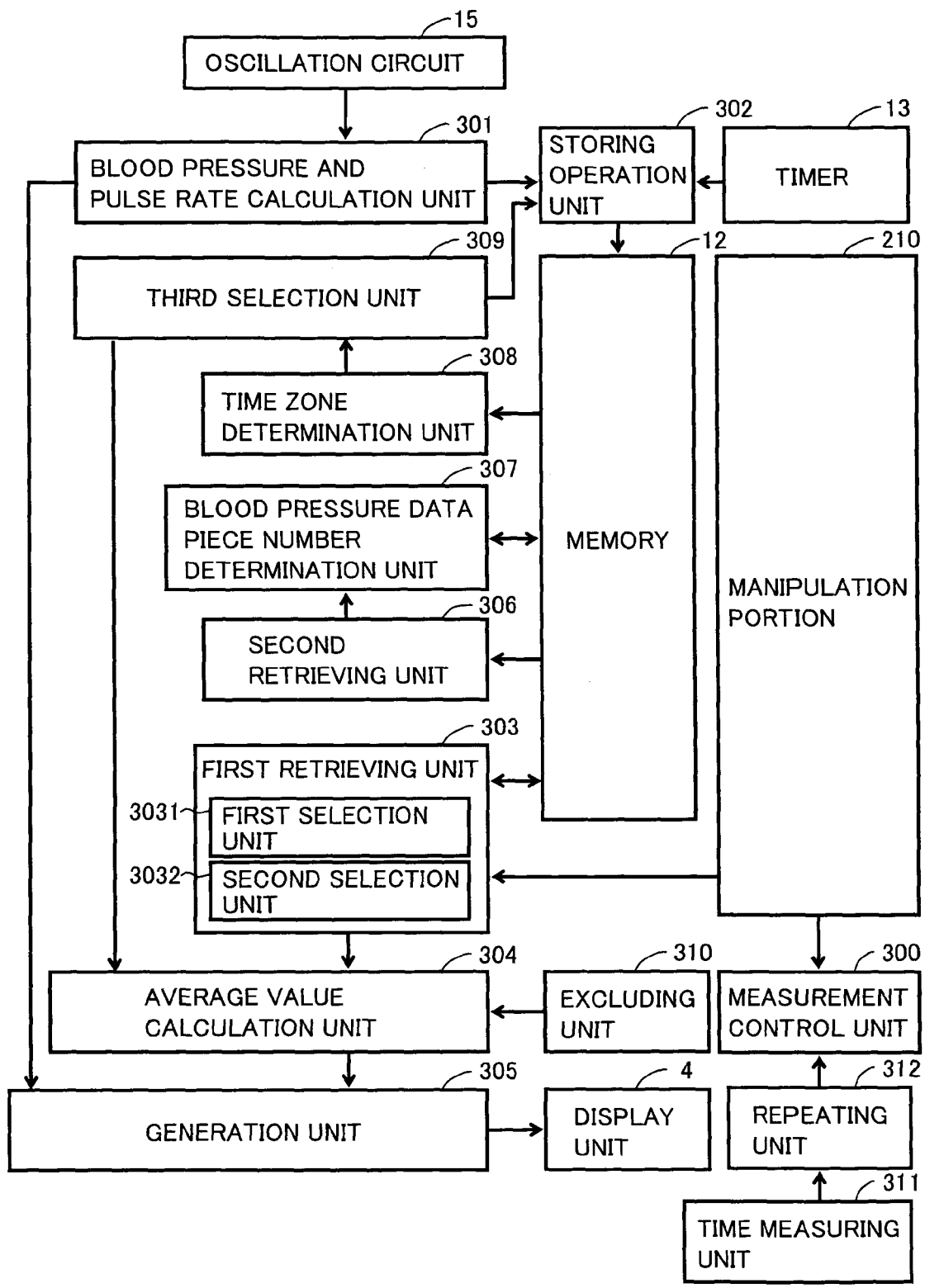
FIG. 18 is a block diagram showing a specific example of a functional configuration of an electronic blood pressure monitor 100.

More specifically, when pressing of memory recall switch 7 is sensed based on a manipulation signal from manipulation portion 210, CPU 20 executes the following processing. FIG. 18 shows a specific example of a functional configuration of electronic blood pressure monitor 100 according to the first embodiment, in execution of the processing. Though the function shown in FIG. 18 is attained mainly in CPU 20 by reading and execution of the program stored in memory 12 by CPU 20, some of these functions may be attained by a hardware configuration shown in FIGS. 1 and 2. Specifically, a first retrieving unit 303 specifies reference measurement data, such as the most recent (immediate) measurement data, among the data of measurement values stored in memory 12 (hereinafter, referred to as "measurement data"), and retrieves measurement data associated with the measurement time within a prescribed time period (for example, 10 minutes) from the measurement time of the reference measurement data. Then, an average value calculation unit 304 calculates the average value based on the retrieved measurement data. A generation unit 305 generates a signal for displaying the calculated average value as the evaluation index. Display unit 4 thus displays the average value as the evaluation index.

In this manner, in the present embodiment, the measurement data associated with the measurement time within a prescribed time period from the measurement time of the reference measurement data is retrieved and selected (extracted) for calculating the average value.

Figure 3:
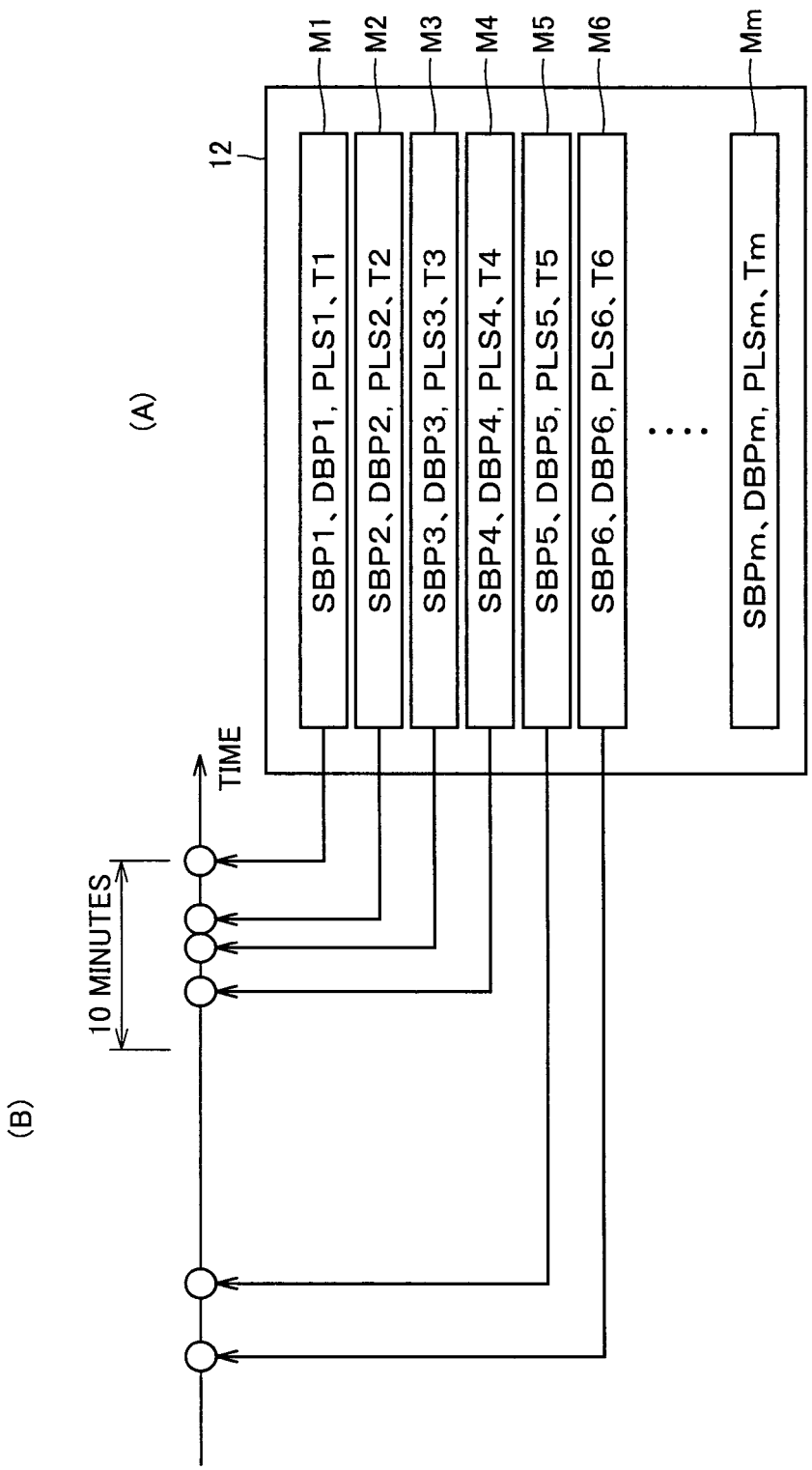
FIG. 3 illustrates, in portion (A), an exemplary data structure in a memory 12 in the first embodiment of the present invention, and shows, in portion (B), a conceptual diagram of measurement data used for calculating an average value in the first embodiment of the present invention.

Referring to portion (A) in FIG. 3, memory 12 stores records obtained by associating the measurement value and the measurement time with each other, as storage data M1 to storage data Mm (m=1, 2, 3, . . . ). In each storage data, systolic blood pressure data SBP representing the systolic blood pressure, diastolic blood pressure data DBP representing the diastolic blood pressure, pulse rate data PLS representing the pulse rate, and measurement time data T are stored. Measurement time data T is stored in the storage data as a result of input of data of a measurement time (time of measurement start or end) timed by timer 13 by CPU 20 and conversion to measurement time data T (year/month/day/hour/minute). It is noted that the measurement value and the measurement time should only be stored in association with each other, and storage is not limited to storage using records.

Referring to portion (B) in FIG. 3, in the present embodiment, the most recent measurement value is stored as storage data M1 each time the blood pressure is measured. Storage data M1 represents the most recent storage data, storage data M2 represents the second storage data, and storage data Mm represents the oldest storage data. Therefore, as shown in portion (B) in FIG. 3, storage data M1 to M4 associated with the measurement time within 10 minutes from the measurement time (T1) of storage data M1 are retrieved and used for calculating the average value.

So far, there has also been a blood pressure monitor which cannot correctly calculate the average value unless measurement is performed three times in the same environment and under the same condition. With such a blood pressure monitor, however, a time period during which the subject is engaged in successive measurement becomes longer, which may become a detriment to blood pressure measurement compliance of the subject.

Therefore, first retrieving unit 303 in FIG. 18 may include a first selection unit 3031 selecting a prescribed plurality of (for example, three) pieces of measurement data associated with the measurement time within 10 minutes from the measurement time of the most recent measurement data, and average value calculation unit 304 may calculate the average value of the selected measurement data. Here, if the number of pieces of retrieved measurement data is smaller than the number of the prescribed plurality of pieces, all retrieved measurement data may be selected and the average value thereof may be calculated. In the description below, it is assumed that CPU 20 calculates the average value of three pieces of past measurement data at the maximum, including the most recent measurement data, that is, three pieces of newest measurement data at the maximum including the most recent measurement data, among the measurement data associated with the measurement time within 10 minutes from the measurement time of the most recent measurement data.

Here, "blood pressure measurement compliance" means intent or motivation to conduct successive blood pressure measurement.

Figure 4A:
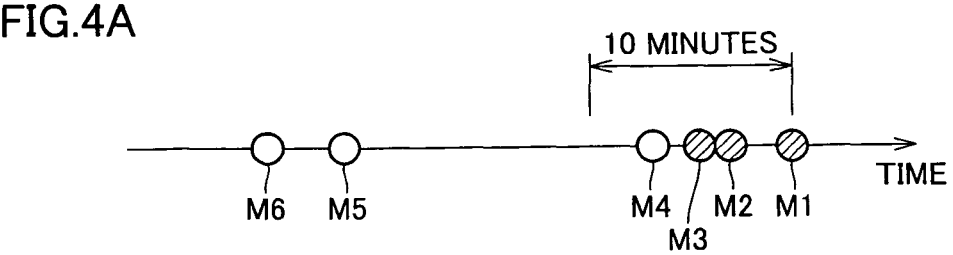
FIGS. 4A to 4C illustrate data selection for calculating an average value in the first embodiment of the present invention.
Figure 4B:
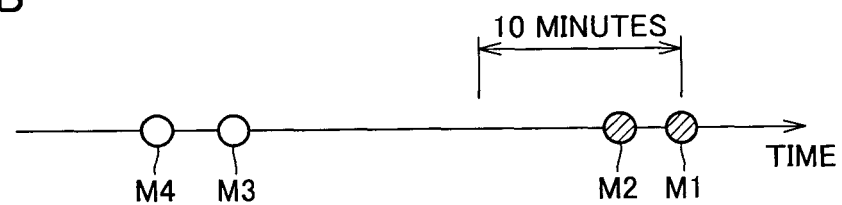
Figure 4C:
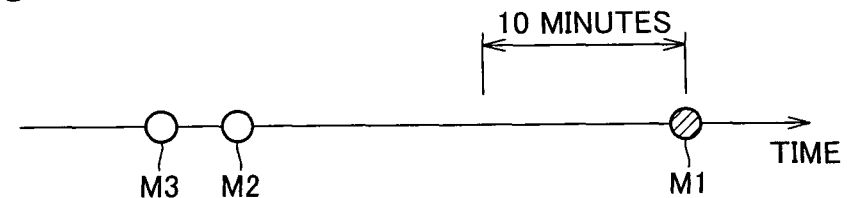

FIGS. 4A to 4C illustrate data selection for calculating an average value in the first embodiment of the present invention. FIG. 4A is a conceptual diagram when measurement is performed three times or more within a prescribed time period (10 minutes). FIG. 4B is a conceptual diagram when measurement is performed twice within a prescribed time period (10 minutes). FIG. 4C is a conceptual diagram when measurement is performed once within a prescribed time period (10 minutes).

Referring first to FIG. 4A, storage data M1 to M4 among storage data M1 to M6 shown along the time-axis are data within 10 minutes from the measurement time (T1) of most recent storage data M1. In the present embodiment, as the average value is calculated using three measurement values at the maximum obtained within the prescribed time period, here, storage data M1 to M3 are selected as the storage data for calculating the average value. The average value of the measurement values of storage data M1 to M3 is calculated using the following equation.

$$SBP\ average=(SBP1+SBP2+SBP3)/3$$

$$DBP\ average=(DBP1+DBP2+DBP3)/3$$

$$PLS\ average=(PLS1+PLS2+PLS3)/3$$

Referring next to FIG. 4B, storage data M1 and M2 among storage data M1 to M4 shown along the time-axis are data within 10 minutes from the measurement time (T1) of most recent storage data M1. In the present embodiment, as the average value is calculated using three measurement values at the maximum obtained within the prescribed time period, here, storage data M1 and M2 are selected as the storage data for calculating the average value. The average value of the measurement values of storage data M1 and M2 is calculated using the following equation.

$$SBP\ average=(SBP1+SBP2)/2$$

$$DBP\ average=(DBP1+DBP2)/2$$

$$PLS\ average=(PLS1+PLS2)/2$$

Referring finally to FIG. 4C, storage data M2 and M3 among storage data M1 to M3 shown along the time-axis are data out of 10-minute range from the measurement time (T1) of most recent storage data M1. In the present embodiment, as the average value is calculated using three measurement values at the maximum obtained within the prescribed time period, here, solely storage data M1 is selected as the storage data for calculating the average value. The average value of the measurement value of storage data M1 is calculated using the following equation.

$$SBP\ average=SBP1$$

$$DBP\ average=DBP1$$

$$PLS\ average=PLS1$$

In this manner, in the present embodiment, even if the subject conducts measurement solely once or twice within the prescribed time period, the average value can be calculated. Therefore, if the subject determines that the average value of the measurement values obtained in measurement conducted twice may be accepted, the average value of the measurement values obtained in measurement conducted twice can be calculated using the algorithm the same as in calculating the average value of three measurement values, by pressing memory recall switch 7 after measurement is conducted twice. Detrimental effect to the blood pressure measurement compliance of the subject can thus be prevented.

In the present embodiment, description will be given assuming that it is predetermined in memory 12 that the reference measurement data (storage data) is the most recent measurement data, however, the reference measurement data is not limited to the most recent measurement data. For example, the reference measurement data may be the oldest measurement data or the measurement data designated by the subject. Here, the expression "designated by the subject" means that the subject has designated the present measurement value as the reference measurement data at the time of blood pressure measurement (before start of blood pressure measurement or at the end of blood pressure measurement). Accordingly, for example, if a not-shown reference data switch is further provided in manipulation portion 210 and a measurement value is obtained by pressing this switch at the time of blood pressure measurement, measurement data corresponding to that measurement value is the "measurement data designated by the subject." In such a case, for example, a storing operation unit 302 in FIG. 18 stores identification information indicating that the data is the designated reference data in memory 12 in association with the measurement data. If the reference data switch is pressed a plurality of times, the measurement data designated last may be employed as the reference measurement data.

Figure 5:
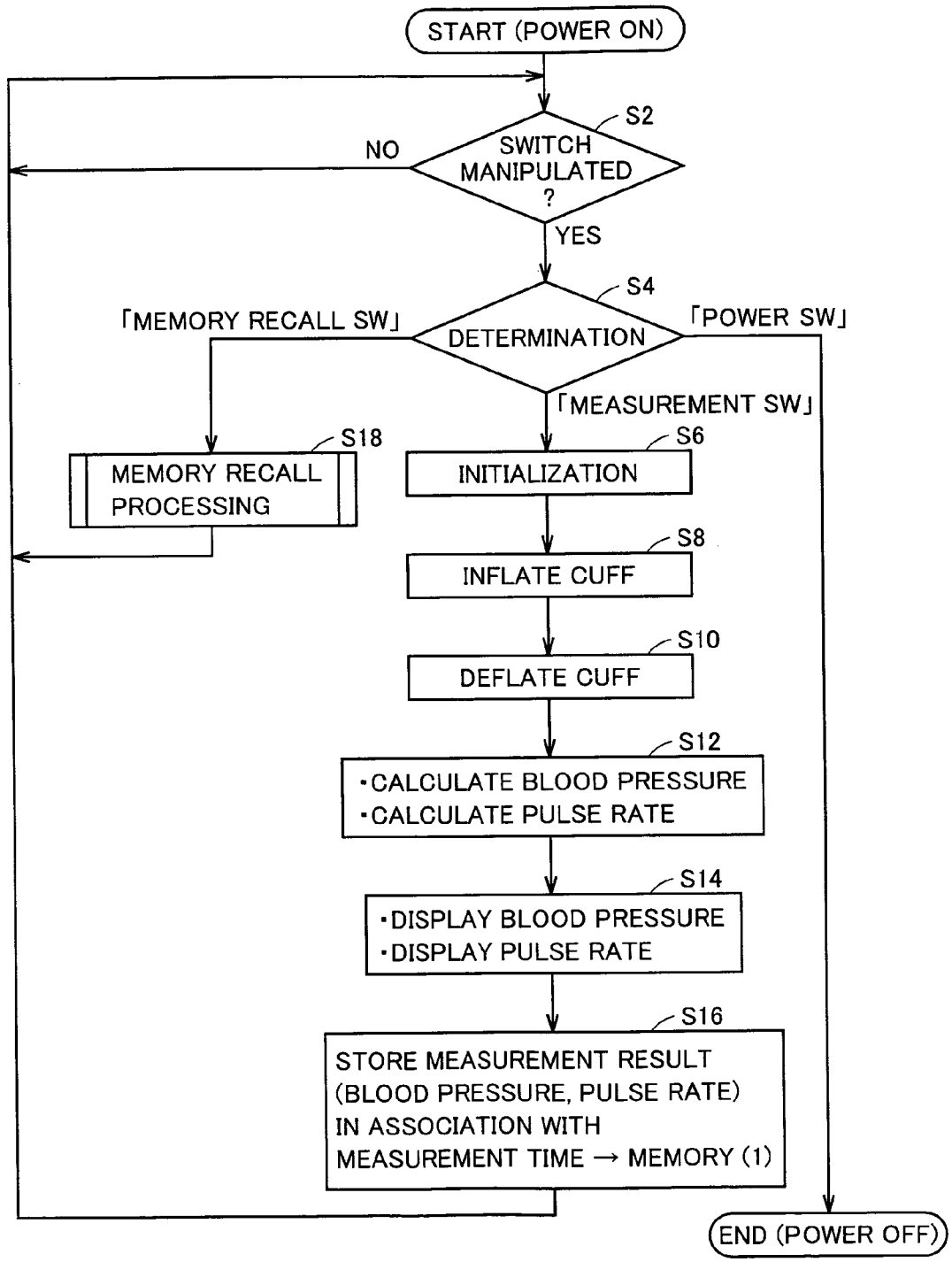
FIG. 5 is a flowchart of a main routine executed by a CPU in the electronic blood pressure monitor according to the first embodiment of the present invention.

The flowchart in FIG. 5 is stored in memory 12 as a program in advance, and executed as a result of reading by CPU 20 and attaining each function in FIG. 18. It is noted that the processing shown in FIG. 5 is the processing started, for example, when power switch 5 is manipulated and power is supplied to CPU 20 through power supply unit 25.

Referring to FIG. 5, initially, CPU 20 determines whether the switch has been manipulated or not (step S (hereinafter, abbreviated as "S") 2). CPU 20 waits until manipulation of the switch is detected (NO in S2). When manipulation of the switch is sensed (YES in S2), the type of the manipulated switch is determined (S4).

When the manipulated switch is determined as measurement switch 6 in S4, the process proceeds to S6. Alternatively, when the manipulated switch is determined as memory recall switch 7, the process proceeds to S18. Further alternatively, when the manipulated switch is determined as power switch 5, the power is turned off and the process ends.

Here, the processing related to measurement of blood pressure shown in S6 to S16 will be described. Initially, a measurement control unit 300 in FIG. 18 controls each component, evacuates air bag 21, and performs 0 mmHg correction of pressure sensor 14 as initialization processing of electronic blood pressure monitor 100 (S6). Thereafter, measurement control unit 300 controls each component, to apply pressure approximately to a level of systolic blood pressure of the subject+40 mmHg (S8). Then, the cuff pressure is gradually reduced (S10). In this pressure reduction process, the cuff pressure is detected by pressure sensor 14. A blood pressure/pulse rate calculation unit 301 calculates the blood pressure (systolic blood pressure and diastolic blood pressure) value and the pulse rate based on the detected pressure (S12). Generation unit 305 generates a signal for displaying the calculated blood pressure value and the pulse rate on display unit 4, for display of the measurement result (S14). The processing for measuring the blood pressure in S8 to S12 is the same as in the conventional electronic blood pressure monitor. Though measurement of blood pressure is conducted in the pressure reduction process, it may be conducted in the pressure application process.

Then, storing operation unit 302 stores the measurement value in memory 12 as storage data M1, in association with the measurement time obtained from timer 13 (S16).

The memory recall processing in S18 will now be described with reference to the subroutine.

Figure 6:
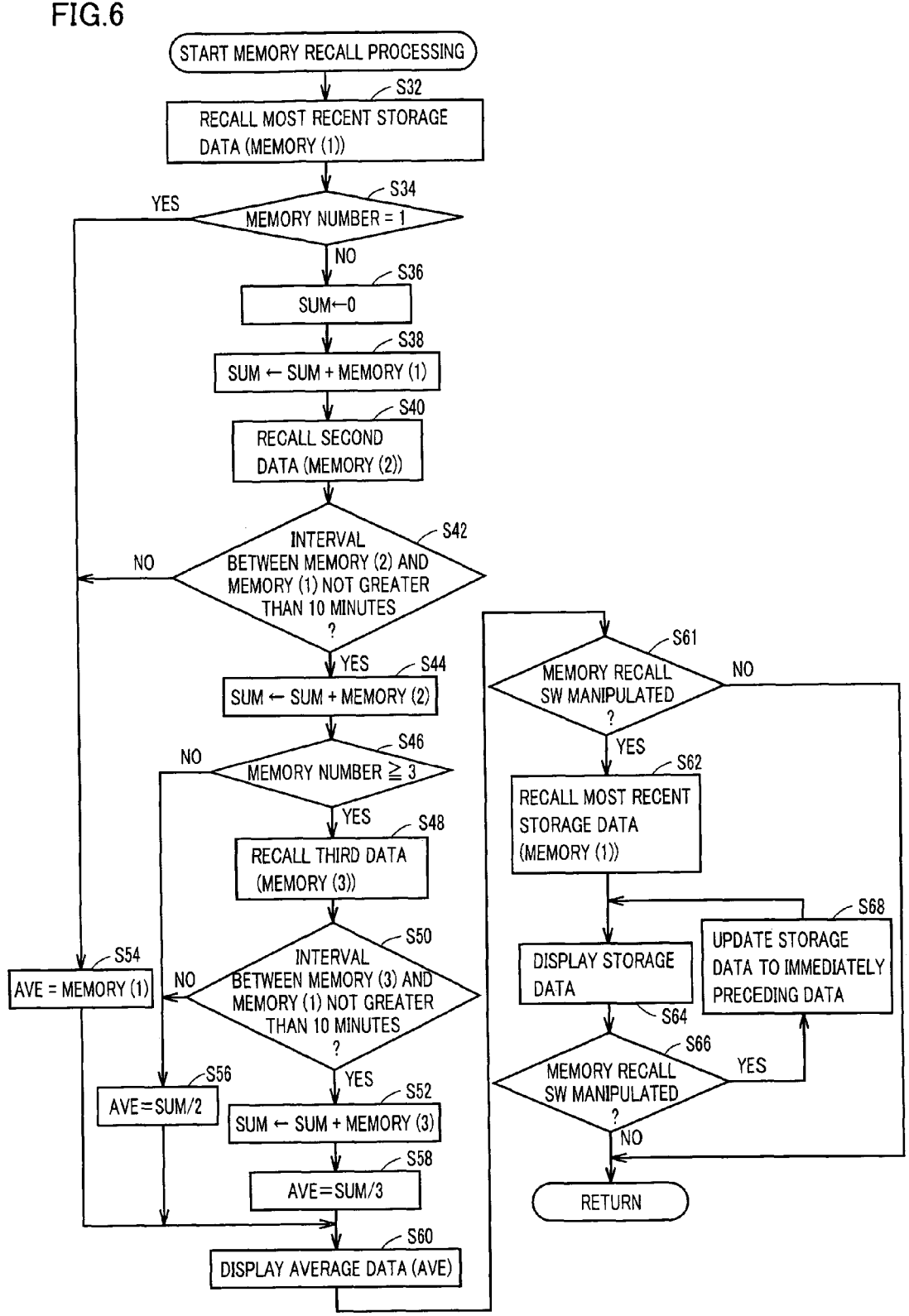
FIG. 6 is a flowchart showing memory recall processing in the first embodiment of the present invention.

The flowchart in FIG. 6 is also stored in memory 12 as a program in advance, and executed as a result of reading by CPU 20 and attaining each function in FIG. 18.

Referring to FIG. 6, initially, first retrieving unit 303 retrieves and recalls the storage data (measurement data) recorded in memory 12 and used as the reference, that is, most recent storage data M1 (S32). Thereafter, a blood pressure data piece number determination unit 307 determines whether the number of pieces of storage data stored in memory 12 (hereinafter, referred to as "memory number") is 1 or not (S34). If it is determined that the memory number is 1, that is, if solely storage data M1 is stored in memory 12 (YES in S34), average value calculation unit 304 calculates an average value AVE as the measurement value of storage data M1 (S54).

If it is determined in step S34 that the memory number is not 1 (NO in S34), average value calculation unit 304 initializes total value SUM used for calculating the average value to "0" (S36). Successively, average value calculation unit 304 adds the measurement value of storage data M1 to total value SUM for update (S38).

Thereafter, first retrieving unit 303 recalls second storage data M2 (S40), and determines whether interval between the measurement time of storage data M2 and the measurement time of storage data M1 is not greater than 10 minutes (S42). If the interval is determined as greater than 10 minutes (NO in S42), the process proceeds to S54 described above. On the other hand, if the interval is determined as not greater than 10 minutes (YES in S42), average value calculation unit 304 adds the measurement value of storage data M2 to total value SUM for update (S44).

Thereafter, blood pressure data piece number determination unit 307 determines whether the memory number is not smaller than 3 (S46). If it is determined that the memory number is less than 3 (NO in S46), average value calculation unit 304 calculates average value AVE of the measurement value of storage data M1 and the measurement value of storage data M2 (S56). More specifically, average value AVE is calculated by dividing total value SUM calculated in step S44 by memory number "2".

If it is determined in step S46 that the memory number is not smaller than 3 (YES in S46), first retrieving unit 303 recalls third storage data M3 (S48), and determines whether interval between the measurement time of storage data M3 and the measurement time of storage data M1 is not greater than 10 minutes (S50). If the interval is determined as greater than 10 minutes (NO in S50), the process proceeds to S56 described above. On the other hand, if the interval between the measurement time of storage data M3 and the measurement time of storage data M1 is determined as not greater than 10 minutes (YES in S50), average value calculation unit 304 adds the measurement value of storage data M3 to total value SUM for update (S52). Then, average value calculation unit 304 calculates average value AVE of the measurement values of storage data M1, storage data M2 and storage data M3 (S58). More specifically, average value AVE is calculated by dividing total value SUM calculated in step S52 by memory number "3".

Then, generation unit 305 generates a signal for displaying average value AVE calculated in any of S54, S56 and S58 on display unit 4, for display of the average value (S60).

Successively, CPU 20 determines whether or not memory recall switch 7 has been manipulated (S61). If it is determined that memory recall switch 7 has been manipulated (YES in S61), the process proceeds to S62. In contrast, if it is determined that memory recall switch 7 has not been manipulated (NO in S61), a series of memory recall processes ends.

In S62, CPU 20 recalls most recent storage data M1 and causes display unit 4 to display the recalled storage data (S64). In addition, CPU 20 determines whether or not memory recall switch 7 has been manipulated (S66). If it is determined that memory recall switch 7 has been manipulated (YES in S66), the storage data is updated to immediately preceding (past) data and this data is recalled (S68). Then, the process returns to S64 described above. In contrast, if it is determined in S66 that memory recall switch 7 has not been manipulated (NO in S66), a series of memory recall processes ends.

Figure 7A:
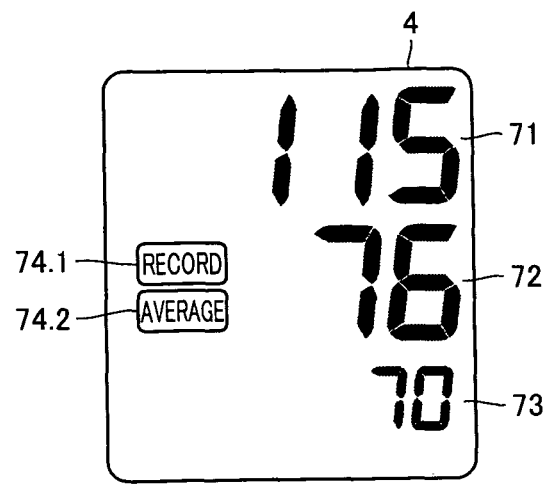
FIG. 7A illustrates an example of display in S60 in FIG. 6.
Figure 7B:
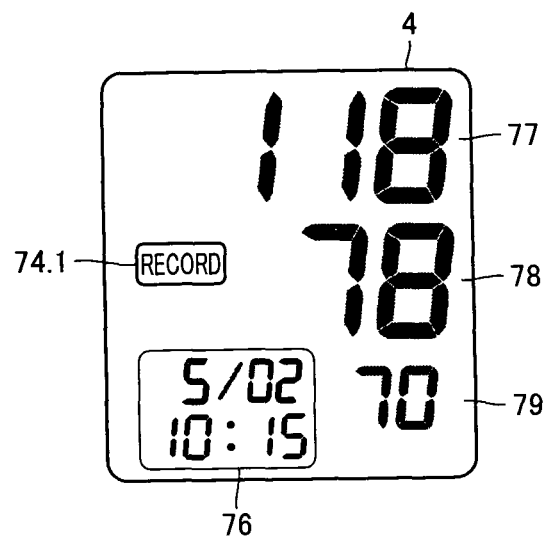
FIG. 7B illustrates an example of display in S64 in FIG. 6.

FIGS. 7A and 7B show display example of the average value or the measurement value displayed on display unit 4 in the first embodiment of the present invention. FIG. 7A illustrates an example of display in S60 in FIG. 6, and FIG. 7B illustrates an example of display in S64 in FIG. 6.

Referring to FIG. 7A, display unit 4 displays information indicating that information on storage data stored in memory 12 is being displayed, for example, text data 74.1 represented by "record", and information indicating that the average value is being displayed, for example, text data 74.2 represented by "average", each in a prescribed display area. Average value AVE calculated in any of S54, S56 and S58, that is, SBP average data 71, DBP average data 72 and PLS average data 73, is displayed in a prescribed display area.

Referring to FIG. 7B, display unit 4 displays text data 74.1 described above, storage data recalled in S62 or S68, that is, SBP data 77, DBP data 78 and PLS data 79, and measurement time data 76 (such as 5/02, 10:15), each in a prescribed display area.

In this manner, as selection of storage data (measurement data) for calculating the average value can be made using solely the information contained in the storage data (systolic blood pressure, diastolic blood pressure, pulse rate, time), influence by the mental and physical condition of the subject or ambient environment can be eliminated with a simplified configuration.

The procedure for retrieving the storage data for calculating the average value is not limited to that as shown in FIG. 6. For example, after the storage data within the 10-minute range is retrieved based on measurement time data T of each storage data, storage data fourth and later may be eliminated.

In addition, in the present embodiment, though measurement data is displayed one by one when memory recall switch 7 is pressed again, a switch for displaying the measurement data one by one may be provided separately.

Moreover, description in the present embodiment has been given, assuming that the number of pieces of measurement data to be selected is set to immediately preceding three at the maximum and the prescribed time period is set to 10 minutes. However, these are by way of example, and other setting may be possible. In addition, description has been given assuming that the number of pieces of measurement data to be selected and the prescribed time are stored, for example, in memory 12 in advance. These values, however, may set by the subject or may be modified.

Further, in the present embodiment, a series of processes for calculating the average value shown in FIG. 6 is performed in response to manipulation of memory recall switch 7, however, the processing in S32 to S60 in FIG. 6 may be performed when measurement of blood pressure ends (after S16 in FIG. 5).

Second Embodiment

A second embodiment of the present invention will now be described. As the configuration of an electronic blood pressure monitor according to the second embodiment is the same as in the first embodiment, description will be given using also the reference numerals of electronic blood pressure monitor 100 shown in FIGS. 1 and 2 and the reference numerals denoting the functions of electronic blood pressure monitor 100 in FIG. 18.

In the first embodiment described above, the average value is calculated based on the measurement data associated with the measurement time within the prescribed time period from the measurement time of the reference (for example, most recent) measurement data stored in memory 12, in response to pressing of memory recall switch 7. In the second embodiment, the average value is calculated based on the measurement data measured within a prescribed time period from the measurement time of the reference measurement data, among the measurement data associated with a time zone in memory 12. That is, in the second embodiment, a condition of a prescribed time zone is added to the condition of the prescribed time period (for example, 10 minutes) in the first embodiment.

In the second embodiment, it is assumed that two time zones such as "morning time zone" and "evening time zone" are predetermined. Manipulation portion 210 further includes morning memory recall switch 9.1 and evening memory recall switch 9.2 for recalling an average value of measurement values measured in these time zones.

It is noted that these time zones may be set by the subject. Alternatively, the subject may be able to change the time zone that has once been set. In addition, the prescribed time zone is not limited to a time zone corresponding to "morning" or "evening", and may be set as any period included in one day (24 hours). For example, a time zone corresponding to "before exercise" or "after exercise" may be set.

In the present embodiment, description will be given assuming that two time zones are set, however, for example, only one time zone may be predetermined and one time zone recall switch for recalling the average value of measurement values obtained in that time zone may be provided. Alternatively, three or more time zones may be predetermined, and a plurality of time zone recall switches for recalling the average value of the measurement values obtained in these time zones may be provided.

In addition, in the present embodiment as well, memory recall switch 7 described in the first embodiment is also provided, however, this switch may not be provided. Namely, solely the measurement data associated with the prescribed time zone (morning time zone, evening time zone) may be selected as the data for calculating the average value.

In the second embodiment, preferably, the reference measurement data among the measurement data associated with the morning time zone is the data obtained immediately after getting up, and for example, the oldest measurement data in the morning time zone is used as the reference measurement data. Meanwhile, the reference measurement data among the measurement data associated with the evening time zone is the data obtained immediately before going to bed, and for example, the most recent measurement data in the evening time zone is used as the reference measurement data.

In addition, in the second embodiment as well, description will be given assuming that the average value of measurement data, for example, three pieces at the maximum, obtained within the prescribed time period from the measurement time of the reference measurement data in each time zone is calculated. It is noted that all measurement data obtained within the prescribed time period from the measurement time of the reference measurement data in each time zone may be selected as the data for calculating the average value.

FIGS. 8A to 8C illustrate data selection for calculating an average value in the second embodiment. FIG. 8A shows a morning time zone and an evening time zone in one day (24 hours), FIG. 8B illustrates data selection for calculating an average value in the morning time zone, and FIG. 8C illustrates data selection for calculating an average value in the evening time zone.

As shown in FIG. 8A, it is assumed that, in electronic blood pressure monitor 100 of the present embodiment, for example, a time zone from 4 o'clock in the morning to 4 o'clock in the next morning (from 4 o'clock in the morning of the previous day to 4 o'clock in the morning of present day) is set as 1 day (24 hours), a time zone from 4 o'clock to 10 o'clock is set as the morning time zone, and a time zone from 16 o'clock to 4 o'clock of the next day is set as the evening time zone, in advance.

Referring to FIG. 8B, it is assumed that blood pressure is measured six times in the morning time zone of one day. Denoting the measurement data in that case as DA1 to DA6 in a reverse chronological order, three pieces of measurement data DA6 to DA4 at the maximum obtained within the prescribed time period (10 minutes) from the measurement time of oldest measurement data DA6 in the morning time zone are selected as the data for calculating the average value in the morning time zone.

Referring to FIG. 8C, it is also assumed that blood pressure is similarly measured six times in the evening time zone of one day. Denoting the measurement data in that case as DB1 to DB6 in a reverse chronological order, three pieces of measurement data DB1 to DB3 at the maximum obtained within the prescribed time period (10 minutes) from most recent measurement data DB1 in the evening time zone are selected as the data for calculating the average value in the evening time zone. As shown in FIG. 8B, though measurement data DB4 is included within the prescribed time period (10 minutes) from the measurement time of most recent measurement data DB1 used as the reference, it is excluded. The algorithm for calculating the average value can thus be simplified.

The flowchart in FIG. 9 is stored in memory 12 as a program in advance, and executed as a result of reading by CPU 20 and attaining each function in FIG. 18. It is noted that the same step number is given to the processing similar to that in FIG. 5.

In the second embodiment, morning memory recall switch 9.1 and evening memory recall switch 9.2 are provided. Therefore, the processing in S84 and S86 is added after the manipulation switch determination processing in S4, and S82 is added after S16.

Referring to FIG. 9, when it is determined in S4 that morning memory recall switch 9.1 has been manipulated, the process proceeds to S84. When it is determined in S4 that evening memory recall switch 9.2 has been manipulated, the process proceeds to S86. After the measurement value is stored in memory 12 in S16, CPU 20 performs the processing for storage for each time zone (S82). Details in these steps S82, S84 and S86 will be described with reference to subroutines.

Figure 10:
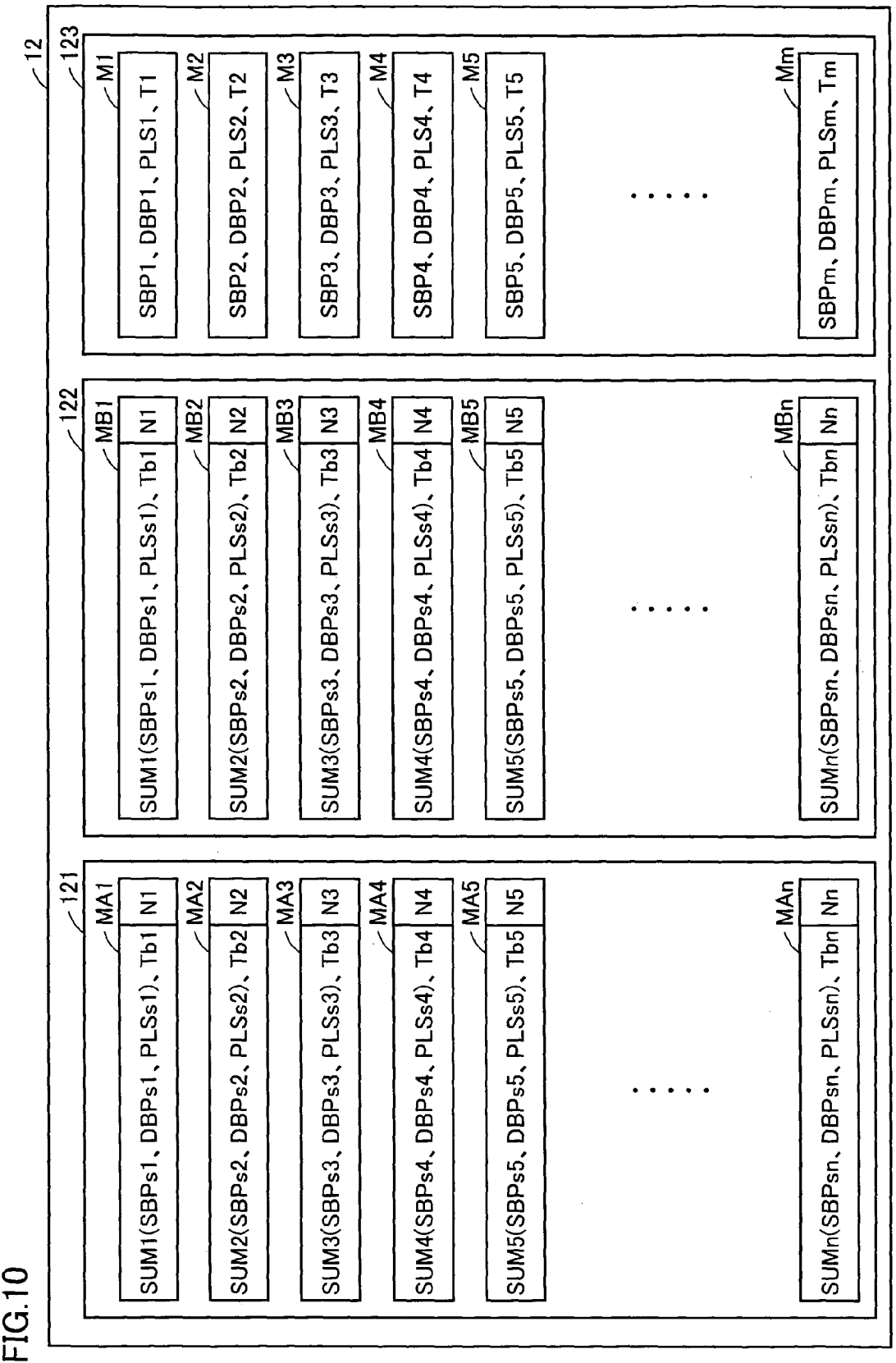
FIG. 10 illustrates an exemplary structure of memory 12 in the second embodiment of the present invention.

FIG. 10 illustrates an exemplary structure of memory 12 in the second embodiment of the present invention.

Referring to FIG. 10, a storage area 121 stores information for calculating the average value in the morning time zone for each day, and a storage area 122 stores information for calculating the average value in the evening time zone for each day. A storage area 123 stores storage data M1 to Mm for each blood pressure measurement, as in the first embodiment.

Storage area 121 stores a record obtained by associating the total value of the measurement values obtained in the morning time zone and selected for calculating the average value with information on the number of pieces of data for each day, as storage data MA1 to MAn in the morning time zone (n=1, 2, 3, . . . ).

Similarly, storage area 122 stores a record obtained by associating the total value of the measurement values obtained in the evening time zone and selected for calculating the average value with information on the number of pieces of data for each day, as storage data MB1 to MBn in the evening time zone (n=1, 2, 3, . . . ).

Each storage data stores total data SUM indicating the total value of the measurement values for calculating the average value, reference time data Tb, and data piece number information N indicating the number of pieces of data. Total data SUM includes data SBPs indicating the total of the systolic blood pressure, data DBPs indicating the total of the diastolic blood pressure data, and data PLSs indicating the total of the pulse rate. In addition, measurement time (T) of the reference measurement data in each time zone is stored as reference time data Tb.

As described above, in the present embodiment, as storage areas 121 and 122 dedicated for each time zone of morning and evening are provided, the measurement data and information on the time zone are stored in association with each other.

Figure 11:
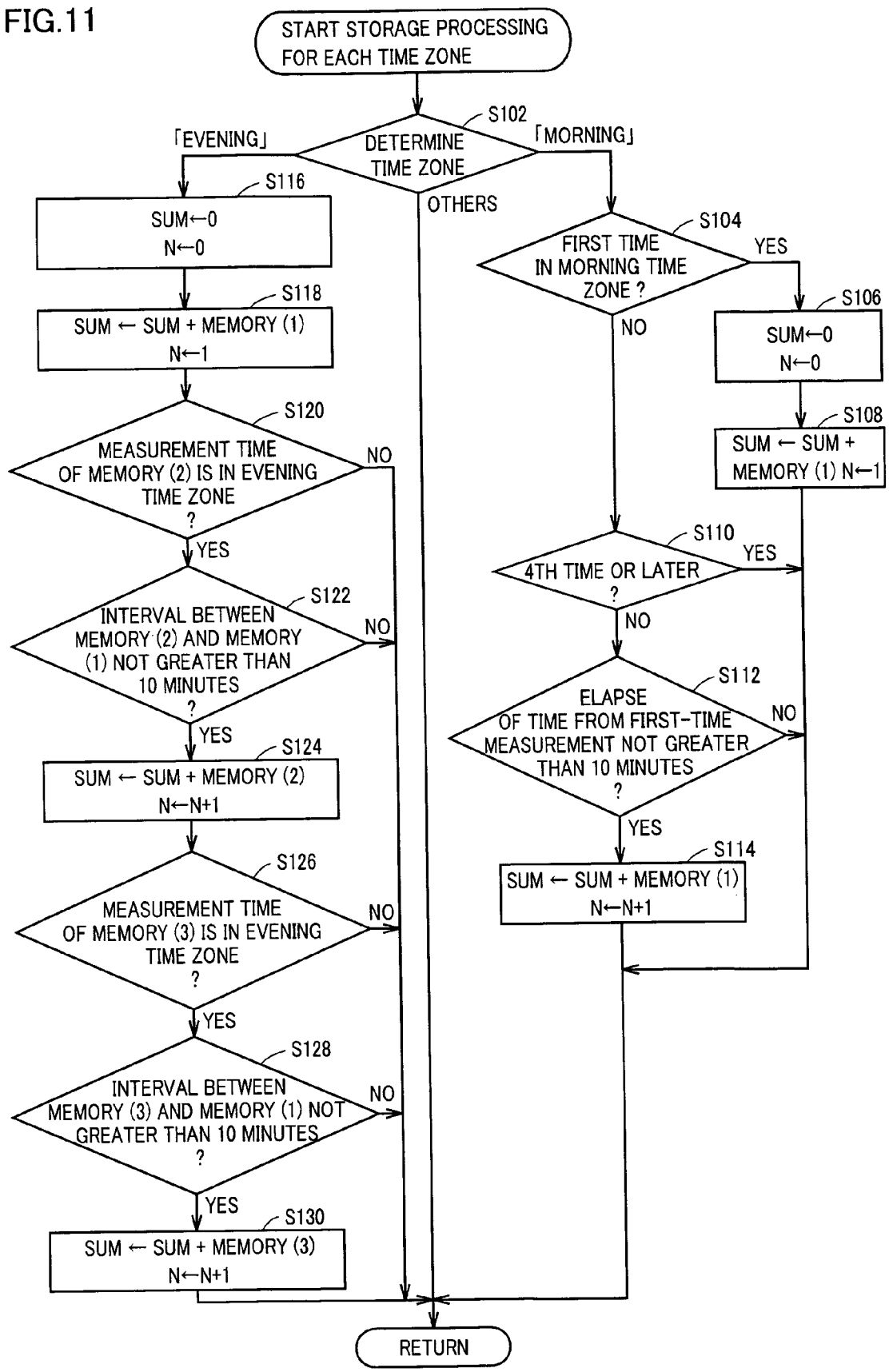
FIG. 11 is a flowchart showing storage processing for each time zone in the second embodiment of the present invention.

FIG. 11 is a flowchart showing storage processing for each time zone (S82).

Initially, a time zone determination unit 308 in FIG. 18 determines the time zone based on measurement time data T stored in association with the measurement value stored in S16 (S102). If the time zone is determined as the morning, the process proceeds to S104. If the time zone is determined as the evening, the process proceeds to S116. If the time zone is determined as other time zone, that is, as a time zone other than morning and evening, the process ends.

In S104, whether or not the present measurement value is the first measurement value in the morning time zone of that day is determined. If the present measurement value is determined as the first measurement value in the morning time zone of that day (YES in S104), average value calculation unit 304 initializes total value SUM of storage data MA1 and data piece number N to "0" (S106). Then, the measurement value of storage data M1 is added to total value SUM, and data piece number N is set to 1 (S108). In S108, measurement time data T of storage data M1 is stored in storage data MA1 as reference time data Tb. After the processing in S108 ends, the process ends.

In S104, if the present measurement value is determined as not the first measurement value in the morning time zone of that day (NO in S104), whether or not the present measurement value is the measurement value fourth or later in the morning time zone of that day is determined (S110). If the present measurement value is determined as the measurement value fourth or later in the morning time zone of that day (YES in S110), the process ends. On the other hand, if the present measurement value is the first, second or third measurement value in the morning time zone of that day (NO in S110), a third selection unit 309 determines whether the interval between the present (most recent) measurement time and the first measurement time is not greater than 10 minutes (S112). If it is determined that the interval is greater than 10 minutes (NO in S112), the process ends. On the other hand, if the interval is determined as not greater than 10 minutes (YES in S112), storing operation unit 302 adds most recent storage data M1 to total value SUM, and increments data piece number N by 1 (S114). After the processing in S114 ends, the process ends.

If the time zone is determined as evening in S102 described above, storing operation unit 302 initializes total value SUM to "0" (S116). In addition, in S116, storing operation unit 302 stores measurement time data T of storage data M1 in storage data MB1 as reference time data Tb. Successively, storing operation unit 302 adds the measurement value of storage data M1 to total value SUM, and sets data piece number N to 1 (S118).

Thereafter, time zone determination unit 308 determines whether or not the measurement time of storage data M2 is in the evening time zone (S120). If it is determined that the measurement time of storage data M2 is not in the evening time zone (NO in S120), that is, if the measurement time of storage data M2 is in the time zone other than the evening time zone or if storage data M2 is not present, the process ends. On the other hand, if it is determined that the measurement time of storage data M2 is in the evening time zone (YES in S120), third selection unit 309 determines whether the interval between the measurement time of storage data M2 and the measurement time of storage data M1 is not greater than 10 minutes (S122). If it is determined that the interval is greater than 10 minutes (NO in S122), the process ends. On the other hand, if it is determined that the interval between the measurement time of storage data M2 and the measurement time of storage data M1 is not greater than 10 minutes (YES in S122), storing operation unit 302 adds the measurement value of storage data M2 to total value SUM, and increments data piece number N by 1 for update (S124).

Successively, time zone determination unit 308 determines whether or not the measurement time of storage data M3 is in the evening time zone (S126). If it is determined that the measurement time of storage data M3 is not in the evening time zone (NO in S126), that is, if the measurement time of storage data M3 is in the time zone other than the evening time zone or if storage data M3 is not present, the process ends. On the other hand, if it is determined that the measurement time of storage data M3 is in the evening time zone (YES in S126), third selection unit 309 determines whether the interval between the measurement time of storage data M3 and the measurement time of storage data M1 is not greater than 10 minutes (S128). If it is determined that the interval is greater than 10 minutes (NO in S128), the process ends. On the other hand, if it is determined that the interval between the measurement time of storage data M3 and the measurement time of storage data M1 is not greater than 10 minutes (YES in S128), storing operation unit 302 adds the measurement value of storage data M3 to total value SUM, and increments data piece number N by 1 (130). After the processing in S130 ends, a series of processes ends.

Figure 12:
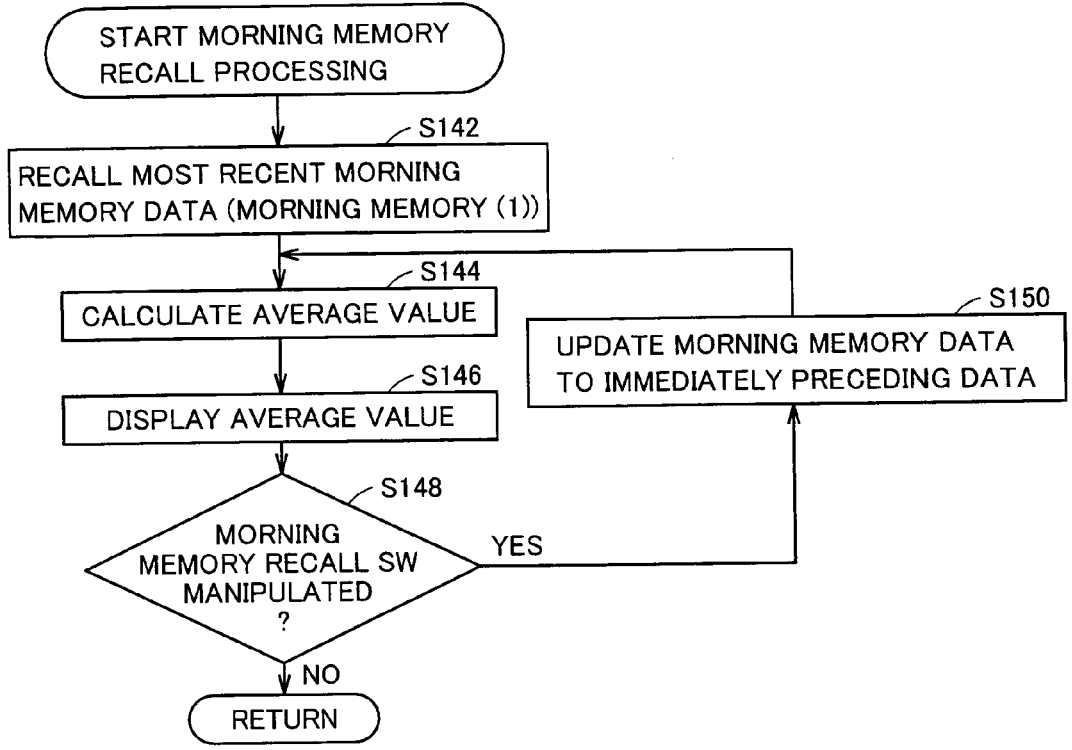
FIG. 12 is a flowchart showing morning memory recall processing in the second embodiment of the present invention.

FIG. 12 is a flowchart showing morning memory recall processing.

Initially, first retrieving unit 303 recalls most recent storage data MA1 in the morning time zone (S142). Then, average value calculation unit 304 calculates the average value based on the recalled storage data of the morning time zone (S144). More specifically, as shown in the equation below, the average value is calculated by dividing total value SUM (SBPs, DBPs, PLSs) by data piece number N.

SBP average=SBPs/$N$

DBP average=DBPs/$N$

PLS average=PLSs/$N$

Then, generation unit 305 generates a signal for displaying the average value calculated in S144 for display (S146).

Thereafter, CPU 20 determines whether or not the morning memory recall switch has been manipulated again (S148). If it is determined that the morning memory recall switch has been manipulated (YES in S148), the morning memory data is updated to immediately preceding (past) data and the updated morning memory data is recalled (S150). After the processing in S150 ends, the process returns to S144 described above.

In S148, if it is determined that the morning memory recall switch has not been manipulated (NO in S148), a series of processes ends.

Figure 13:
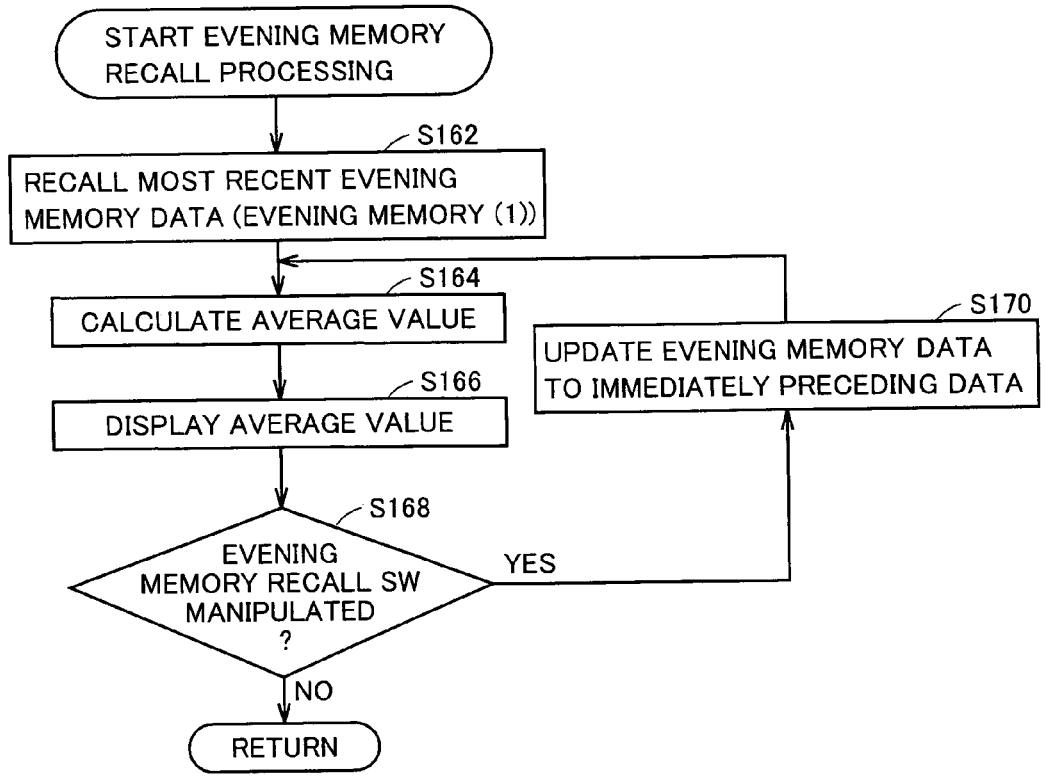
FIG. 13 is a flowchart showing evening memory recall processing in the second embodiment of the present invention.

FIG. 13 is a flowchart showing evening memory recall processing.

Initially, first retrieving unit 303 recalls most recent storage data MB1 in the evening time zone (S162). Then, average value calculation unit 304 calculates the average value based on the recalled storage data of the evening time zone (S164). More specifically, the average value is calculated by dividing total value SUM (SBPs, DBPs, PLSs) by data piece number N, as in S144. Then, generation unit 305 generates a signal for displaying the average value calculated in S164 for display (S166).

Thereafter, CPU 20 determines whether or not the evening memory recall switch has been manipulated again (S168). If it is determined that the evening memory recall switch has been manipulated (YES in S168), the evening memory data is updated to immediately preceding data and the updated evening memory data is recalled (S170). After the processing in S170 ends, the process returns to S164 described above.

In S168, if it is determined that the evening memory recall switch has not been manipulated (NO in S168), a series of processes ends.

Figure 14A:
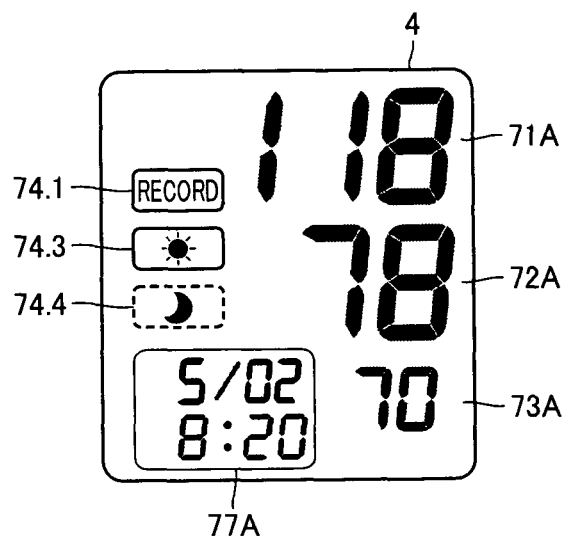
FIG. 14A illustrates an example of display in S146 in FIG. 12.
Figure 14B:
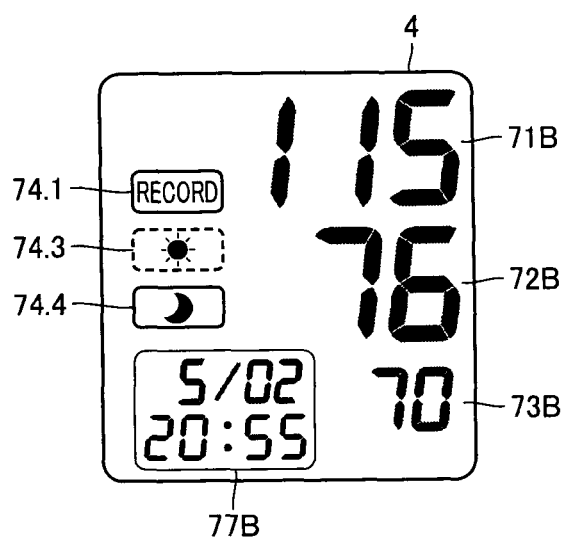
FIG. 14B illustrates an example of display in S166 in FIG. 13.

FIG. 14A illustrates an example of display in S146 in FIG. 12, and FIG. 14B illustrates an example of display in S166 in FIG. 13.

Referring to FIG. 14A, display unit 4 displays text data 74.1 described above, and information indicating that the average value in the morning time zone is being displayed, for example, mark 74.3 represented by "morning", each in a prescribed display area, and display unit 4 displays in gray, information indicating that the average value in the evening time zone is being displayed, for example, mark 74.4 represented by "evening" in a prescribed display area. The average value calculated in S144, that is, SBP average data 71A, DBP average data 72A and PLS average data 73A, is displayed in a prescribed display area. In addition, reference time (Tb) data 77A of the corresponding storage data is displayed in a prescribed display area.

Referring to FIG. 14B, display unit 4 displays text data 74.1 described above and mark 74.4 indicating that the average value in the evening time zone is being displayed, and display unit 4 displays in gray, mark 74.3 indicating that the average value in the morning time zone is being displayed. Then, the average value calculated in S164, that is, SBP average data 71B, DBP average data 72B and PLS average data 73B, is displayed. In addition, reference time (Tb) data 77B of the corresponding storage data is displayed in the prescribed display area.

In the second embodiment, the storage areas for the morning time zone and the evening time zone are provided in memory 12, so that information for calculating the average value in each time zone is stored. The configuration, however, may be such that these storage areas are not provided. In such a case, as in the first embodiment, storage data M1 to Mm are stored in memory 12 for each blood pressure measurement, and for example, when morning memory recall switch 9.1 is pressed, the average value in the most recent morning time zone may be calculated based on measurement time data T of each storage data.

If storage data in the past morning time zone is displayed as a result of pressing of morning memory recall switch 9.1 several times and thereafter evening memory recall switch 9.2 is pressed, the storage data in the evening time zone of the same day or the previous day may immediately be recalled. That is, if evening memory recall switch 9.2 is pressed successively after morning memory recall switch 9.1 is pressed, the average value of the storage data in the evening time zone of the same day or the previous day of the day of measurement of the storage data of which average value has been calculated immediately before (last) (the evening time zone corresponding to immediately before or after the morning time zone of the day of measurement of the storage data of which average value has been calculated last) may be calculated.

In contrast, if storage data in the past evening time zone is displayed as a result of pressing of evening memory recall switch 9.2 several times and thereafter morning memory recall switch 9.1 is pressed, the storage data in the morning time zone of the same day or the next day may immediately be recalled. That is, if morning memory recall switch 9.1 is pressed successively after evening memory recall switch 9.2 is pressed, the average value of the storage data in the morning time zone of the same day or the next day of the day of measurement of the storage data of which average value has been calculated immediately before (last) (the morning time zone corresponding to immediately before or after the evening time zone of the day of measurement of the storage data of which average value has been calculated last) may be calculated.

Third Embodiment

A third embodiment of the present invention will now be described. As the configuration of an electronic blood pressure monitor according to the third embodiment is the same as in the first embodiment, description will be given using also the reference numerals of electronic blood pressure monitor 100 shown in FIGS. 1 and 2 and the reference numerals denoting the functions of electronic blood pressure monitor 100 shown in FIG. 18.

In the first embodiment, among the measurement data associated with the measurement time within the prescribed time period (10 minutes) from the measurement time of the reference measurement data such as the most recent measurement data, three pieces of measurement data at the maximum including the most recent measurement data are selected and the average value thereof is calculated. In the third embodiment, the measurement data for calculating the average value is selected based not on the number of pieces of data but on the value of each measurement data.

In the third embodiment, in order to calculate the average value, an allowable range of fluctuation from the reference measurement value (blood pressure value and pulse rate) is set in advance, for example, in memory 12. Then, first retrieving unit 303 in FIG. 18 includes a second selection unit 3032 selecting the measurement value within the allowable range of fluctuation from the reference measurement value, and average value calculation unit 304 calculates the average value of the measurement values selected by second selection unit 3032. The allowable fluctuation range may be set and modified by the subject.

In the present embodiment, for example, the measurement value corresponding to the reference measurement data, such as the oldest measurement data, is employed as the reference measurement value. Here, the reference measurement data may be the most recent measurement data or the measurement data designated by the subject.

Figure 15A:
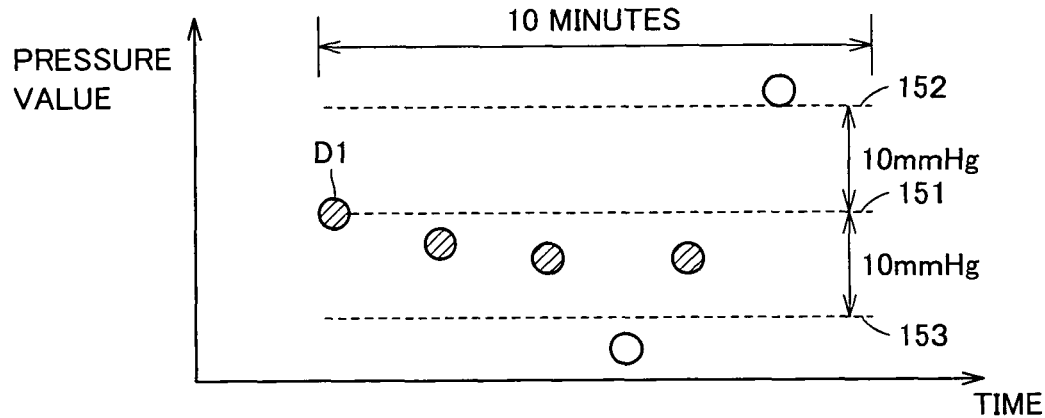
FIGS. 15A and 15B illustrate data selection for calculating an average value in a third embodiment of the present invention.
Figure 15B:
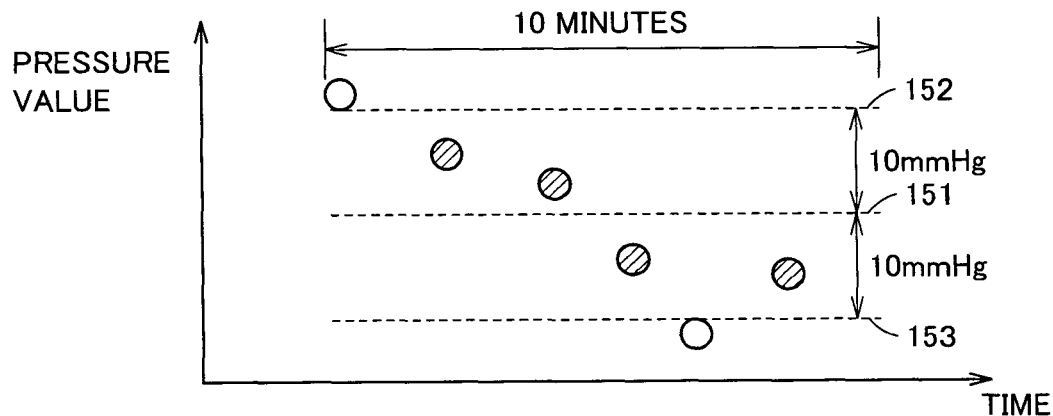

FIGS. 15A and 15B show an exemplary allowable fluctuation range of the blood pressure value, in which the abscissa represents the time and the ordinate represents the pressure value.

As shown in FIG. 15A, it is assumed that the allowable fluctuation range is set in advance as a range ±10 mmHg from the blood pressure value of the oldest measurement data D1. Then, solely the blood pressure data between a line 152 at the level of +10 mmHg from a line 151 in parallel to the abscissa indicating the blood pressure value of the oldest measurement data D1 and a line 153 at the level of −10 mmHg from line 151 is selected as the data for calculating the average value. Blood pressure data outside the allowable fluctuation range is excluded, even if it is the data within the 10-minute range. Here, determination as to whether or not the data is within the allowable fluctuation range is made for each of the systolic blood pressure, the diastolic blood pressure and the pulse rate.

In the third embodiment, for example, whether the interval between the measurement time of storage data M2 and the measurement time of storage data M1 is not greater than 10 minutes and whether or not the data is within the allowable fluctuation range may be determined, for example, in S42 in the flowchart shown in FIG. 6. Similarly, such determination may be made in S50.

In addition, the reference measurement value is not limited to the measurement value corresponding to the reference measurement data. For example, as shown in FIG. 15B, the average value (provisional average value) of the measurement values (blood pressure values) within the prescribed time period (10 minutes) may be calculated and the provisional average value may be employed as the reference measurement value. That is, the blood pressure data within a range between lines 152 and 153 extending along a level ±10 mmHg from line 151 used as the reference indicating the provisional average value is selected as the data for calculating the average value. Solely the measurement data selected in this manner is used to calculate the ultimate average value.

Whether or not the measurement data stored in memory 12 is within the allowable fluctuation range is determined as described above, however, second retrieving unit 306 in FIG. 18 may determine whether or not data is within the allowable fluctuation range for each blood pressure measurement. Here, for example, second retrieving unit 306 retrieves the measurement data stored in association with the measurement time within the prescribed time period from the measurement time of the obtained measurement data, and blood pressure data piece number determination unit 307 determines whether or not a prescribed plurality of (for example, three) pieces of measurement data within the prescribed allowable range of fluctuation from the reference blood pressure are present, among the retrieved measurement data. If it is determined that the prescribed plurality of pieces of data are not present, buzzer 24 may give alarm sound or display unit 4 may give prescribed display, so as to urge the subject to conduct measurement again.

Alternatively, if it is determined that the prescribed plurality of pieces of data are not present, the processing in S6 to S16 shown in FIG. 5 may be repeated until it is determined that the prescribed plurality of pieces of data are present.

Further alternatively, the average value may be calculated only after a prescribed plurality of pieces of measurement data within the allowable range are present. Further, the average value may be calculated after a prescribed time (10 minutes) has passed, even though there are not a prescribed plurality of pieces of data.

Determination as to whether or not the data is within such an allowable fluctuation range may be made with regard to the measurement data in the prescribed time zone described in the second embodiment.

Fourth Embodiment

A fourth embodiment of the present invention will now be described. As the configuration of an electronic blood pressure monitor according to the fourth embodiment is the same as in the first embodiment, description will be given using also the reference numerals of electronic blood pressure monitor 100 shown in FIGS. 1 and 2.

In the first embodiment, among the measurement data associated with the measurement time within the prescribed time period (10 minutes) from the measurement time of the reference measurement data such as the most recent measurement data, three pieces of measurement data at the maximum including the most recent measurement data are selected and the average value thereof is calculated. In the fourth embodiment, if CPU 20 senses interruption of continuity within a prescribed time period, the average value is calculated using solely the measurement data before or after sensing of interruption. For example, if the most recent measurement data is employed as the reference measurement data, the average value is preferably calculated by selecting the measurement data after sensing of interruption, excluding the measurement data before sensing of interruption. If the oldest measurement data is employed as the reference measurement data, the average value is preferably calculated by selecting the measurement data before sensing of interruption, excluding the measurement data after sensing of interruption.

In the fourth embodiment, in order to sense interruption of continuity, electronic blood pressure monitor 100 includes, for example, an electrode 31 for detecting placement/removal of cuff 2 and a signal sensing unit 32 for sensing a signal from electrode 31. Electrode 31 is provided, for example, in a hook and loop fastener (not shown) for holding cuff 2 wrapped around the measurement site, and signal sensing unit 32 is provided in blood pressure monitor main unit 1. Electrode 31 and signal sensing unit 32 are connected to each other, for example, through a cable set coaxially with air tube 3.

A potential of electrode 31 is varied when the hook and loop fastener is fastened or released, and signal sensing unit 32 senses whether or not the potential has been varied. When signal sensing unit 32 senses potential variation, it supplies a signal to CPU 20. Upon receiving the signal from signal sensing unit 32, CPU 20 obtains a time from timer 13 and records the obtained time (year/month/day/hour/minute), for example, in memory 12, as the time of interruption. The processing by signal sensing unit 32 may be performed by CPU 20.

Then, when memory recall switch 7 is pressed, an excluding unit 310 in FIG. 18 determines whether or not the time of interruption stored in memory 12 is within 10-minute range from the measurement time of the most recent measurement data. If it is determined that the time of interruption is within the 10-minute range, measurement data before the time of interruption is excluded. That is, average value calculation unit 304 calculates the average value by selecting the measurement data present between the measurement time of the most recent measurement data and the time of interruption, in accordance with the result of determination in excluding unit 310.

Figure 16:
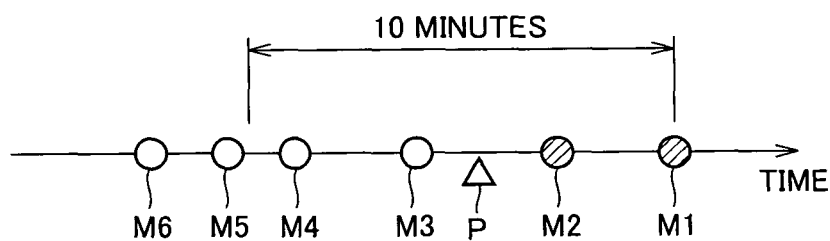
FIG. 16 illustrates data selection for calculating an average value in a fourth embodiment of the present invention.

Data selection for calculating an average value in the fourth embodiment will be described with reference to FIG. 16. Referring to FIG. 16, it is assumed that storage data M1 to M4 among storage data M1 to M6 shown along the time-axis are storage data within the 10-minute range. If placement/removal of cuff 2 is sensed between storage data M2 and storage data M3, that is, if time of interruption P is present between the measurement time of storage data M2 and the measurement time of storage data M3, (measurement data of) storage data M1 and M2 are selected as the data for calculating the average value.

In the fourth embodiment, for example, whether the interval between the measurement time of storage data M2 and the measurement time of storage data M1 is not greater than 10 minutes and whether or not the data was obtained before the time of interruption may be determined, for example, in S42 in the flowchart shown in FIG. 6. Similarly, such determination may be made in S50.

In this manner, fluctuation of blood pressure due to variation in the mental and physical condition of the subject or the ambient environment can further sufficiently be eliminated.

In the description above, interruption of continuity is sensed based on placement/removal of cuff 2, however, sensing of interruption of continuity is not limited as such. For example, an ON/OFF operation of power switch 5 included in manipulation portion 210 may be considered as interruption of continuity. Here, CPU 20 records in memory 12, as the time of interruption, the time when an ON/OFF signal from power switch 5 is received, and the processing thereafter can be performed in a manner the same as in the case of placement/removal of cuff 2.

Alternatively, an opening/closing operation of cover 10B may be considered as interruption of continuity. Here, for example, an opening/closing sensor 30 for detecting opening/closing of cover 10B may be provided in a locking portion of cover 10B in blood pressure monitor main unit 1 (see FIG. 1). In this case, CPU 20 records in memory 12, as the time of interruption, the time when opening/closing of cover 10B is sensed based on a detection signal from opening/closing sensor 30, and the processing thereafter can be performed in a manner the same as in the case of placement/removal of cuff 2. It is noted that opening/closing sensor 30 may be provided, for example, in a hinge portion of cover 10B. Alternatively, a switch is provided in the locking portion of cover 10B instead of opening/closing sensor 30, and CPU 20 may sense opening/closing of cover 10B based on an ON/OFF signal from the switch.

Selection of measurement data within the prescribed time period included in the prescribed time zone described in the second embodiment may be made also based on sensing of interruption of continuity as described above.

Fifth Embodiment

A fifth embodiment of the present invention will now be described. As the configuration of an electronic blood pressure monitor according to the fifth embodiment is the same as in the first embodiment, description will be given using also the reference numerals of electronic blood pressure monitor 100 shown in FIGS. 1 and 2.

Electronic blood pressure monitor 100 according to the fifth embodiment attains a measurement-at-intervals function, and calculates the average value of the measurement values obtained by measurement-at-intervals.

For example, memory 12 stores information on a time interval and information on the number of times of measurement in advance. A time measuring unit 311 in FIG. 18 finds the time interval based on time data output from timer 13 and counts the number of times of measurement. A repeating unit 312 monitors counting by time measuring unit 311, and transmits a signal to measurement control unit 300 such that blood pressure measurement (S6 to 16) is repeated each time prescribed time interval elapses, until the count attains to the prescribed number of times of measurement.

In the present embodiment, such measurement-at-intervals may be completed within a prescribed period (10 minutes).

In addition, in the first to fourth embodiments above, description has been given assuming that the prescribed period is determined in advance or determined by the subject. In the present embodiment, however, the prescribed time period may be determined as follows.

A method of setting a prescribed time period in the fifth embodiment of the present invention will be described with reference to FIG. 17. In the present embodiment, it is assumed that the time interval for measurement-at-intervals and the number of times of measurement can be set by the subject. Such setting may be made, for example, by further providing a dedicated switch (not shown) and manipulating this switch. Alternatively, setting may be made in such a manner that a setting menu for measurement-at-intervals is displayed on display unit 4 when power switch 5 is turned on and a prescribed switch such as memory recall switch 7 or time setting switch 8 is manipulated. The prescribed time period is determined by multiplying the set time interval by the number of times of measurement.

Figure 17:
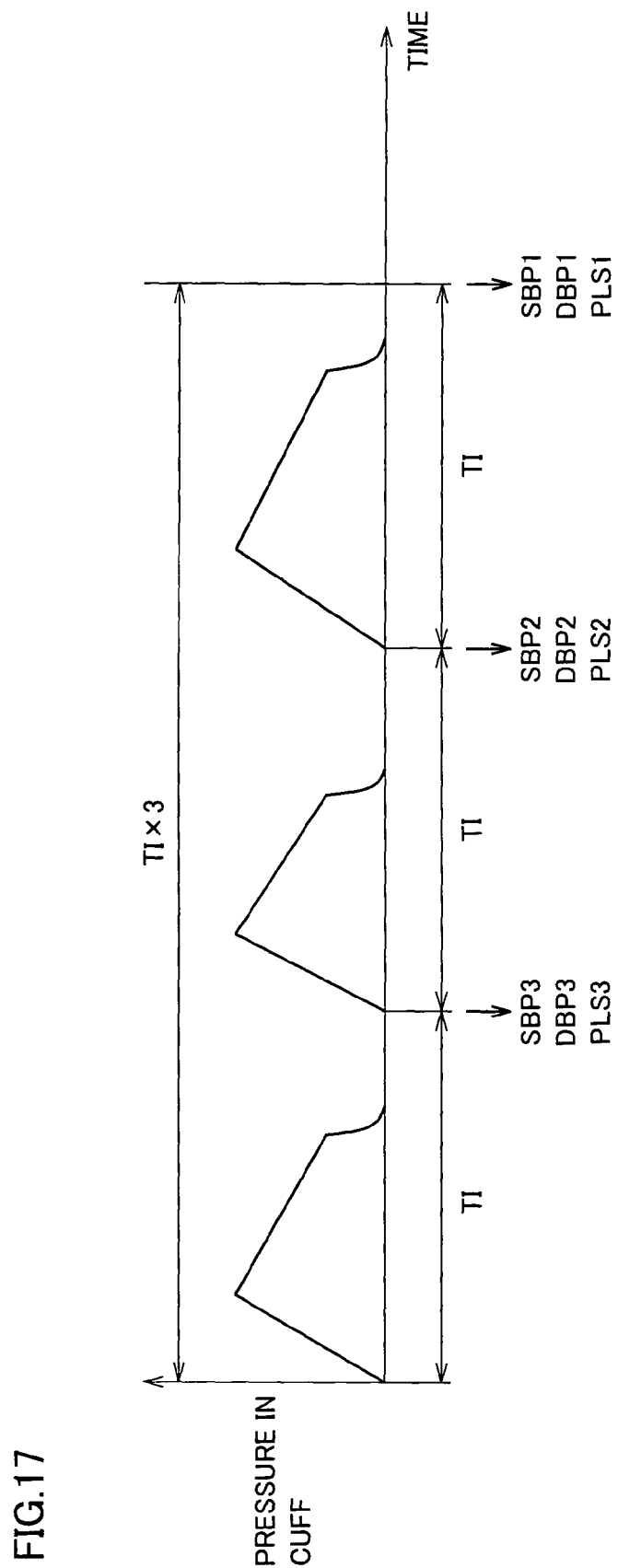
FIG. 17 illustrates a method of setting a prescribed time period in a fifth embodiment of the present invention.

Referring to FIG. 17, for example, it is assumed that the time interval for measurement-at-intervals is set as time TI and the number of times of measurement is set to 3. Then, the prescribed time period is calculated as TI×3.

The average value calculating processing for the measurement values measured in such measurement-at-intervals can be performed, using the equation below.

SBP average=(SBP1+SBP2+SBP3)/3

DBP average=(DBP1+DBP2+DBP3)/3

PLS average=(PLS1+PLS2+PLS3)/3

In the embodiments of the present invention described above, description has been given using an upper-arm blood pressure monitor by way of example, which assumes the upper arm as the measurement site. The present invention, however, is also applicable to any blood pressure monitor placed on limbs, such as a wrist blood pressure monitor.

In addition, the method of calculating an average value performed by the electronic blood pressure monitor according to the present invention may be provided as a program. Such a program can be recorded on a computer-readable recording medium such as an optical medium including a CD-ROM (Compact Disk-ROM) and a memory card, and can be provided as a program product. Alternatively, the program may be provided by downloading through the network.

The provided program product is installed in a program storage unit such as a hard disk for execution. It is noted that the program product includes the program itself and the recording medium recording the program.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An electronic blood pressure monitor, comprising:
a measurement unit for measuring blood pressure of a subject and generating blood pressure data;
a time counting unit for counting time;
a memory for storing the measured blood pressure data in association with information related to a measurement time;
a manipulation portion configured to be manipulated by said subject;
a first retrieving unit for retrieving, as specific data, blood pressure data associated with a measurement time within a prescribed time period measured from a measurement time of predetermined reference blood pressure data from among the blood pressure data stored in said memory, the reference data being part of the measured and stored blood pressure data, wherein said first retrieving unit includes a first selection unit for selecting a prescribed number of pieces of blood pressure data from among the specific data, where, if the prescribed number of pieces is greater than the total number of pieces of specific data, the selection unit selects all of the specific data to serve as the selected prescribed number of pieces of blood pressure data;
an average value calculation unit for calculating an average value based on adding together said selected pieces of blood pressure data and said reference blood pressure data;
a generation unit generating a signal for displaying said calculated average value as an evaluation index;
and a display unit for displaying a display corresponding to said signal generated by said generation unit.

2. The electronic blood pressure monitor according to claim 1, wherein
it is predetermined that said reference blood pressure data is most recent blood pressure data among the blood pressure data stored in said memory, and
said first retrieving unit retrieves, as said specific data, blood pressure data associated with a measurement time within said prescribed time period from a measurement time of said most recent blood pressure data.

3. The electronic blood pressure monitor according to claim 1, wherein
it is predetermined that said reference blood pressure data is oldest blood pressure data among the blood pressure data stored in said memory, and
said first retrieving unit retrieves, as said specific data, blood pressure data associated with a measurement time within said prescribed time period from a measurement time of said oldest blood pressure data.

4. The electronic blood pressure monitor according to claim 1, wherein
it is predetermined that said reference blood pressure data is blood pressure data designated by said subject, among the blood pressure data stored in said memory, and
said first retrieving unit retrieves, as said specific data, blood pressure data associated with a measurement time within said prescribed time period from a measurement time of said designated blood pressure data.

5. The electronic blood pressure monitor according to any one of claims 2 to 4, wherein
said manipulation portion includes a manipulation switch provided in order to recall information on the blood pressure data stored in said memory, and
said reference blood pressure data is specified in response to pressing of said manipulation switch.

6. The electronic blood pressure monitor according to claim 1, further comprising:
a second retrieving unit for retrieving, as intended blood pressure data, blood pressure data stored in association with a measurement time within said prescribed time period from said measurement time of said measured blood pressure data for each blood pressure measurement;
a blood pressure data piece number determination unit for determining whether a prescribed plurality of pieces of blood pressure data within a prescribed allowable range of fluctuation from the reference blood pressure data are present among said intended blood pressure data; and
a notification unit for urging measurement again upon said subject if said blood pressure data piece number determination unit determines that there are not as many blood pressure data as said prescribed plurality of pieces.

7. The electronic blood pressure monitor according to claim 1, further comprising:
a second retrieving unit for retrieving, as intended blood pressure data, blood pressure data stored in association with a measurement time within said prescribed time period from said measurement time of said measured blood pressure data for each blood pressure measurement; and
a blood pressure data piece number determination unit for determining whether a prescribed plurality of pieces of blood pressure data within a prescribed allowable range of fluctuation from the reference blood pressure data are present among said intended blood pressure data;
wherein measurement of blood pressure by said measurement unit is repeated until said blood pressure data piece number determination unit determines that said prescribed plurality of pieces of blood pressure data are present.

8. The electronic blood pressure monitor according to claim 6 or 7, wherein it is predetermined that said reference blood pressure data is blood pressure data corresponding to any one of oldest blood pressure data, most recent blood pressure data, and blood pressure data designated by said subject, among said intended blood pressure data.

9. The electronic blood pressure monitor according to claim 1, further comprising:
a sensing unit for sensing interruption of continuity among a plurality of pieces of blood pressure data measured within said prescribed time period; and
an excluding unit for excluding from said specific data, blood pressure data before or after a time at which said interruption is sensed by said sensing unit;
wherein said average value calculation unit calculates an average value of the blood pressure data after exclusion by said excluding unit.

10. The electronic blood pressure monitor according to claim 9, wherein
said measurement unit includes
a cuff that can be placed on a blood pressure measurement site,
a pressure application/reduction unit for regulating a pressure to be applied to said cuff,
a pressure detection unit for detecting a pressure in said cuff, and
a blood pressure calculation unit for calculating blood pressure based on a signal obtained in said pressure detection unit, and
said sensing unit senses placement or removal of said cuff as said interruption of continuity.

11. The electronic blood pressure monitor according to claim 9, wherein said sensing unit senses an ON/OFF signal from said manipulation portion as said interruption of continuity.

12. The electronic blood pressure monitor according to claim 9, further comprising a cover connected to a main unit of said electronic blood pressure monitor in a freely opening/closing manner, wherein said sensing unit senses opening/closing of said cover as said interruption of continuity.

13. The electronic blood pressure monitor according to claim 1, further comprising:
a first time zone determination unit for determining whether a measurement time is included in a prescribed time zone for each blood pressure measurement;
a selection unit for selecting blood pressure data measured within said prescribed time period from a measurement time of said reference blood pressure data, if said first time zone determination unit determines that the measurement time is included in said prescribed time zone; and
a storing operation unit for storing blood pressure data selected by said second selection unit in said memory in association with said prescribed time zone.

14. The electronic blood pressure monitor according to claim 13, wherein
it is predetermined that said reference blood pressure data is most recent blood pressure data in said prescribed time zone among the blood pressure data stored in said memory, and
said storing operation unit stores a prescribed plurality of pieces of blood pressure data in said memory sequentially from said most recent blood pressure data in a reverse chronological order.

15. The electronic blood pressure monitor according to claim 13, wherein
it is predetermined that said reference blood pressure data is oldest blood pressure data in said prescribed time zone among the blood pressure data stored in said memory, and
said storing operation unit stores a prescribed plurality of pieces of blood pressure data in said memory sequentially from said oldest blood pressure data in a chronological order.

16. The electronic blood pressure monitor according to claim 14 or 15, wherein said storing operation unit stores all blood pressure data measured in said prescribed time zone in said memory, if number of pieces of blood pressure data measured in said prescribed time zone is smaller than number of said prescribed plurality of pieces of blood pressure data.

17. The electronic blood pressure monitor according to claim 1, further comprising:
a time zone determination unit for determining whether the measurement time is included in any one of a first time zone and a second time zone for each blood pressure measurement;
a second selection unit for selecting, as said specific data, blood pressure data measured within said prescribed time period from the measurement time of said reference blood pressure data and within said first time zone if said time zone determination unit determines that the measurement time is included in said first time zone; and
a storing operation unit for storing said specific data selected by said second selection unit in said memory in association with a measurement day and said first time zone.

18. The electronic blood pressure monitor according to claim 17, wherein
said manipulation portion includes a first manipulation switch associated with said first time zone and a second manipulation switch associated with said second time zone that are provided to recall an average value of said specific data associated with each of said time zones in said memory,
wherein when said first manipulation switch is pressed, said average value calculation unit further calculates an average value of the stored data in said first time zone, and
wherein when said second manipulation switch is pressed after said first manipulation switch is pressed, said average value calculation unit further calculates an average value of the stored data in said second time zone in any of the same day, next day, and previous day of a day of measurement of the specific data that was averaged as being part of the first time zone.

19. The electronic blood pressure monitor according to claim 1, wherein said prescribed time period can be set by said subject.

20. The electronic blood pressure monitor according to claim 1, further comprising:
a time measuring unit for measuring a prescribed time interval based on time data from said time counting unit; and
a repeating unit for repeating blood pressure measurement by said measurement unit at prescribed times, each time said prescribed time interval elapses within said prescribed time period.

21. The electronic blood pressure monitor according to claim 20, further comprising a setting unit for setting the time interval and number of times of blood pressure measurement in said repeating unit;
wherein said prescribed time period is a time period determined based on said time interval and said number of times.

* * * * *